(12) United States Patent
Duclos et al.

(10) Patent No.: US 8,722,656 B2
(45) Date of Patent: May 13, 2014

(54) CEPHALOSPORINS USEFUL AS ANTIBACTERIAL AGENTS

(75) Inventors: Brian A. Duclos, Kalamazoo, MI (US); Edmund L. Ellsworth, Portage, MI (US); Richard A. Ewin, Kalamazoo, MI (US); Paul D. Johnson, Kalamazoo, MI (US); Timothy A. Johnson, Richland, MI (US); Graham M. Kyne, Portage, MI (US); Susan M. K. Sheehan, Galesburg, MI (US); Rajendran Vairagoundar, Kalamazoo, MI (US)

(73) Assignee: Zoetis LLC, Florham Park, NJ (US)

( * ) Notice: Subject to any disclaimer, the term of this patent is extended or adjusted under 35 U.S.C. 154(b) by 0 days.

(21) Appl. No.: 13/459,851

(22) Filed: Apr. 30, 2012

(65) Prior Publication Data

US 2012/0283237 A1    Nov. 8, 2012

Related U.S. Application Data

(60) Provisional application No. 61/481,407, filed on May 2, 2011.

(51) Int. Cl.
*A61K 31/545* (2006.01)
*C07D 501/60* (2006.01)

(52) U.S. Cl.
USPC .......................................... 514/207; 540/230

(58) Field of Classification Search
USPC .............................. 540/215, 219; 514/206, 207
See application file for complete search history.

(56) References Cited

U.S. PATENT DOCUMENTS

| | | | |
|---|---|---|---|
| 2,776,992 | A | 1/1957 | Gregory |
| 3,294,818 | A | 12/1966 | Bobowski et al. |
| 4,235,892 | A | 11/1980 | Nagabhushan |
| 4,311,857 | A | 1/1982 | Nagabhushan |
| 4,361,557 | A | 11/1982 | Nagabhushan |
| 5,114,933 | A | 5/1992 | Bertrandie et al. |
| 5,721,359 | A | 2/1998 | Dunn et al. |
| 7,041,670 | B2 | 5/2006 | Boojamra et al. |
| 7,153,842 | B2 | 12/2006 | Hecker et al. |
| 7,361,689 | B2 | 4/2008 | Shuster et al. |
| 7,518,017 | B2 | 4/2009 | Murthy et al. |
| 7,572,777 | B2 | 8/2009 | Hecker et al. |
| 7,713,950 | B2 | 5/2010 | Shuster et al. |
| 7,786,329 | B2 | 8/2010 | Towson |
| 2007/0155799 | A1 | 7/2007 | Glinka et al. |
| 2008/0146640 | A1 | 6/2008 | Glinka |
| 2008/0153906 | A1 | 6/2008 | Celly et al. |
| 2008/0188556 | A1 | 8/2008 | Glinka et al. |
| 2008/0319200 | A1 | 12/2008 | Towson |
| 2009/0170954 | A1 | 7/2009 | Towson et al. |
| 2010/0210851 | A1 | 8/2010 | Towson |
| 2010/0331376 | A1 | 12/2010 | Towson et al. |

FOREIGN PATENT DOCUMENTS

| | | |
|---|---|---|
| EP | 0 061 234 | 9/1982 |
| EP | 0 295 341 | 12/1988 |
| WO | 2007/145656 | 12/2007 |

OTHER PUBLICATIONS

PCT International Search Report, PCT/IB2012/051973, mailed Jun. 22, 2012 (4 pages).
Lee et al., "Synthesis and Antibacterial Activities of Novel C(3)-Aminopyrimidinyl Substituted Caphalosporins Including Against Respiratory Tract Pathogens", Bioorganic & Medicinal Chemistry Letters, 10:2123-2127, 2000.
"US FDA 21 CFR Part 530: New Animal Drugs; Cephalosporin Drugs; Extralabel Animal Drug Use; Order of Prohibition", Federal Register, vol. 77, No. 4, Jan. 6, 2012, pp. 735-745.

*Primary Examiner* — Noble Jarrell
*Assistant Examiner* — Laura Daniel
(74) *Attorney, Agent, or Firm* — Martha A. Gammill

(57) ABSTRACT

The present invention provides novel cephalosporin derivatives of formula I,

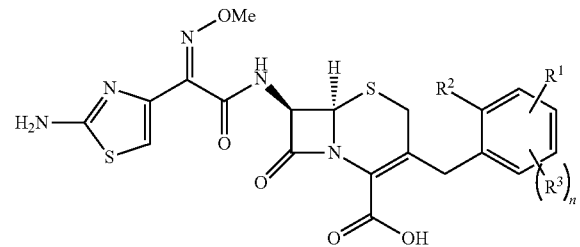

their analogues, their use for the treatment of infections in mammals, pharmaceutical composition containing these novel compounds, and methods for the preparation of these compounds.

17 Claims, No Drawings

CEPHALOSPORINS USEFUL AS ANTIBACTERIAL AGENTS

CROSS-REFERENCE TO RELATED APPLICATIONS

This application claims the benefit of priority to U.S. Provisional Application No. 61/481,407 filed May 2, 2011.

FIELD OF THE INVENTION

The present invention provides novel cephalosporin derivatives, their analogues, their use for the treatment of infections in mammals, pharmaceutical composition containing these novel compounds, and methods for the preparation of these compounds.

BACKGROUND OF THE INVENTION

Cephalosporins are broad spectrum, commonly used antibacterial agents for the treatment of bacterial infections. The emergence and spread of resistance to second and third generation cephalosporins is threatening to create species resistance to all currently available agents. Resistant bacteria populations are increasing because of the combined impact of the various uses of antimicrobial drugs in humans and animals, including the use of expanded-spectrum cephalosporins. In the field of animal health, particularly in food-producing animals, while cephalosporins are currently used for the treatment of various infections, there are considerable regulatory and public concerns around the use of second and third generation cephalosporins due to the concern that the resistant organisms, particularly the resistant organisms of *Escherichia coli*, *Salmonella* and *Campylobacter*, will be transferred to human health as contaminants in foodstuffs. Accordingly, there remains a demand for alternative novel cephalosporins that have selective spectrum of antibacterial efficacy to the targeted pathogens with minimal or no activity against unintended pathogens to minimize the development of resistant organisms. A pharmaceutical or veterinary product of this nature would have a minimal impact to human, animals and environment. The present invention provides novel cephalosporin derivatives that are selective against infections in mammals caused by pathogens such as *Mannheimia haemolytica*, *Pasteurella multocida*, and *Histophilus somni*.

SUMMARY OF THE INVENTION

The present invention provides a compound of formula I:

or a pharmaceutically acceptable salt thereof wherein:
$R^1$ is $-NR^4R^5$, $-SO_2R^6$, $-C(=O)NR^4R^4$, $-SR^4$, $-S(C=O)R^4$, $-S(C=S)R^4$, $-SC(=O)OR^4$, $-SC(=O)NHR^4$, $-SP(=O)(OR_4)_2$; or $R^1$ is $-C_{1-8}$alkyl substituted with $-SR^4$, $-S(C=O)R^4$, $-S(C=S)R^4$, $-SC(=O)OR^4$, $-SC(=O)NHR^4$, $-SP(=O)(OR_4)_2$, $-C(=O)NR^4R^5$, $-SO_2R^6$; or $R^1$ is $-OC_{1-8}$alkyl substituted with $-SR^4$, $-S(C=O)R^4$, $-S(C=S)R^4$, $-SC(=O)OR^4$, $-SC(=O)NHR^4$, $-SP(=O)(OR_4)_2$, $-C(=O)NR^4R^5$, or $-SO_2R^6$;

$R^2$ and $R^3$ are independently $-H$, $-OH$, $-CN$, halo, $-NO_2$, $-C_{1-10}$alkyl, $-OC_{1-10}$alkyl, $-N(R^4)_2$;

or $R^1$ and $R^3$ taken together with the carbons to which they are attached form an aryl or heteroaryl;

$R^4$ is $-H$ or $-C_{1-10}$alkyl;

$R^5$ is $-SO_2R^{4^*}$, $-C(=O)C_{1-10}$alkyl;

$R^6$ is H, $C_{1-6}$alkyl, or $NR^4R^4$;

at each occurrence, $C_{1-10}$alkyl is optionally substituted with $-OH$, $-CN$, halo, $-NO_2$, $-OC_{1-6}$alkyl, $-SH$, $-SC_{1-4}$alkyl, $-S(C=O)C_{1-4}$alkyl, or $-O(C=O)C_{1-4}$alkyl; and n is 1, 2, or 3.

In another aspect, the present invention also provides:

pharmaceutical compositions which comprise a pharmaceutically acceptable carrier and a compound of formula I, methods for controlling or treating infections in mammals caused by Gram-negative respiratory pathogens by administering to a mammal in need of a therapeutically effective amount of a compound of formula I or a pharmaceutically acceptable salt thereof, methods for controlling or treating infections in livestock caused by Gram-negative pathogens by administering to a mammal in need a therapeutically effective amount of a compound of formula I or a pharmaceutically acceptable salt thereof, methods for treatment of infections in mammal caused by Gram-negative pathogens such as *Mannheimia haemolytica*, *Pasteurella multocida*, and *Histophilus somni*, methods for treating infections in cattle and swine caused by Gram-negative pathogens such as *Mannheimia haemolytica*, *Pasteurella multocida*, and *Histophilus somni*, methods for treating bovine respiratory disease caused by Gram-negative respiratory pathogens such as *Mannheimia haemolytica*, *Pasteurella multocida*, and *Histophilus somni*, methods for treating swine respiratory disease caused by Gram-negative respiratory pathogens such as *Mannheimia haemolytica*, *Pasteurella multocida*, and *Histophilus somni*, and methods for the preparation of compounds of the present invention.

DETAILED DESCRIPTION

With respect to the above compound, and throughout the application and claims, the following terms have the meanings defined below.

The term "halo" refers to chloro, bromo, fluoro, and iodo.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-4}$ alkyl refers to alkyl of one to four carbon atoms, inclusive; $C_{1-6}$ alkyl refers to alkyl of one to six carbon atoms, inclusive; $C_{1-8}$ alkyl refers to alkyl of one to eight carbon atoms, inclusive; $C_{1-10}$ alkyl refers to alkyl of one to ten carbon atoms, inclusive.

The term alkyl refers to straight, branched and a cyclic saturated monovalent hydrocarbon groups, but reference to an individual radical such as "propyl" embraces only the straight chain radical, a branched chain isomer such as "isopropyl" or a cyclic isomer such as cyclopropylmethyl or cyclopentyl being specifically referred to.

The term "aryl" refers to a cyclic or polycyclic aromatic ring having from 5 to 12 carbon atoms, and optionally substituted with 1-3 groups selected from —OH, —CN, halo, —NO$_2$, C$_{1-4}$alkyl, —OC$_{1-6}$alkyl, —SH, —SC$_{1-4}$alkyl, —S(C=O)C$_{1-4}$alkyl, or —O(C=O)C$_{1-4}$alkyl.

The term "heteroaryl" refers to an aromatic cyclic or polycyclic ring system having from 1 to 3 hetero atoms selected from N, O, and S. Heteroaryl is optionally substituted with 1-3 groups selected from —OH, —CN, halo, —NO$_2$, C$_{1-4}$alkyl, —OC$_{1-6}$alkyl, —SH, —SC$_{1-4}$alkyl, —S(C=O)C$_{1-4}$alkyl, or —O(C=O)C$_{1-4}$alkyl. Typical heteroaryl groups include 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl. Preferred aromatic fused heterocyclic rings of from 8 to 10 atoms include but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

The term "mammal" refers to human or animals including livestock and companion animals. The phrase "companion animal" or "companion animals" refers to animals kept as pets. Examples of companion animals include cats, dogs, and horses. The term "livestock" refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys. Specifically, livestock animals of the present invention refer to cattle and pigs.

The term "controlling", "treating" or "treatment" of a disease includes: (1) preventing the disease, i.e. causing the clinical symptoms or signs of the disease not to develop in a mammal that may be exposed to or predisposed to the disease but does not yet experience or display symptoms/signs of the disease; (2) inhibiting the disease, i.e., arresting or reducing the development of the disease or its clinical symptoms/signs; or (3) relieving the disease, i.e., causing regression of the disease or its clinical symptoms/signs.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "pharmaceutically acceptable" means suitable for use in mammals, companion animals or livestock animals.

The term "prodrug" refers to a bio-reversible derivative of a molecule, i.e. a compound of formula I of the present invention. Prodrugs can alter the solubility, lipophilicity and in-vivo distribution of drugs. By deliberately altering these key properties, it may be possible to improve absorption, enhance onset time, reduce first pass metabolism, allow development of aqueous IV formulations and achieve targeted delivery. In addition, prodrugs are useful in improving transdermal delivery, masking taste, minimizing pain on injection, improving stability, etc. In situations where the pharmacophore itself leads to poor delivery properties, prodrugs are one of the few strategies that can be used to salvage the highly active compound. Included within the scope of the present invention are all prodrugs of the compounds of formula I that can be prepared by the standard methods known to one skilled in the art. Prodrugs of the compounds of formula I may be prepared following the methods described in "Prodrugs of phosphates, phosphonates, and phosphinates", Krise J P, Stella V J, Advanced Drug Delivery Reviews, 19: (2) 287-310 May 22 1996; "Targeted Prodrug Design to Optimize Drug Delivery". Hyo-Kyung Han and Gordon Amidon. AAPS PharmSci 2000; 2 (1) article 6; "Prodrugs", L. Prokai and K. Prokai-Tatrai, Chapter 12 in *Injectable Drug Development: Techniques to Reduce Pain and Irritation*, Interpharm Press, Buffalo Grove, Ind., 1999; "Improved oral drug delivery: Solubility limitations overcome by the use of prodrugs", Fleisher D, Bong R, Stewart B H, Advanced Drug Delivery Reviews, 19: (2) 115-130 May 22 1996; or "Preparation and hydrolysis of water soluble, non-irritating prodrugs of pharmaceuticals with oxaalkanoic acids", Crooks, Peter Anthony; Cynkowski, Tadeusz; Cynkowska, Grazyna; Guo, Hong; Ashton, Paul. PCT Int. Appl. (2000), 65 pp.

Compounds that have the same molecular formula but differ in the nature or sequence of bonding of their atoms or the arrangement of their atoms in space are termed "isomers".

Included within the scope of the described compounds are all isomers (e.g. cis-, trans-, enantiomers, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds.

Specifically, the compounds of the present invention are compounds of formula I wherein $R^1$ is —NR$^4$R$^5$, —SO$_2$R$^6$, —C(=O)NR$^4$R$^4$, —SR$^4$, —S(C=O)R$^4$, —C$_{1-4}$alkyl substituted with —SR$^4$, —S(C=O)R$^4$, —C(=O)NR$^4$R$^5$, or —SO$_2$R$^6$; or $R^1$ is —OC$_{1-8}$alkyl substituted with —SR$^4$, —S(C=O)R$^4$, —C(=O)NR$^4$R$^5$, or —SO$_2$R$^6$.

Specifically, the compounds of the present invention are compounds of formula I wherein $R^1$ is —NR$^4$R$^5$, —SO$_2$R$^6$, or —C$_{1-4}$alkyl substituted with —SR$^4$, —S(C=O)R$^4$, —C(=O)NR$^4$R$^5$, or —SO$_2$R$^6$.

Specifically, the compounds of the present invention are compounds of formula wherein $R^1$ is —C$_{1-4}$alkyl substituted with —SR$^4$, —S(C=O)R$^4$, or —SO$_2$R$^6$.

Specifically, the compounds of the present invention are compounds of formula wherein A compound of claim 1 wherein $R^1$ a methyl substituted with —SR$^4$, —S(C=O)R$^4$ or —SO$_2$R$^6$.

Specifically, the compounds of the present invention are compounds of formula wherein $R^1$ a methyl substituted with —SH, or —S(C=O)CH$_3$.

Specifically, the compounds of the present invention are compounds of formula wherein $R^1$ is —NHC$_{1-6}$alkyl substituted —SH, —SC$_{1-4}$alkyl, or —S(C=O)C$_{1-4}$alkyl.

Specifically, the compounds of the present invention are compounds of formula I wherein $R^2$ is H or C$_{1-4}$alkyl.

Specifically, the compounds of the present invention are compounds of formula I wherein $R^2$ is C$_{1-4}$alkyl.

Specifically, the compounds of the present invention are compounds of formula I wherein $R^3$ is H, OH, or C$_{1-6}$alkyl optionally substituted with OH, CN, halo, NO$_2$, OC$_{1-6}$alkyl, SH, SC$_{1-4}$alkyl, S(C=O)C$_{1-4}$alkyl, or —O(C=O)C$_{1-4}$alkyl.

Specifically, the compounds of the present invention are compounds of formula I wherein $R^3$ is H or C$_{1-4}$alkyl optionally substituted with OH, OC$_{1-4}$alkyl, SH, or SC$_{1-4}$alkyl.

Specifically, the compounds of the present invention are compounds of formula I wherein $R^1$ is —$NR^4R^5$, —$SO_2R^6$, —C(=O)$NR^4R^4$, —$SR^4$, —S(C=O)$R^4$, —$C_{1-4}$alkyl substituted with —$SR^4$, —S(C=O)$R^4$, —C(=O)$NR^4R^5$, or —$SO_2R^6$; or $R^1$ is —$OC_{1-8}$alkyl substituted with —$SR^4$, —S(C=O)$R^4$, —C(=O)$NR^4R^5$, or —$SO_2R^6$; $R^2$ is H or $C_{1-4}$alkyl; and $R^3$ is H or $C_{1-4}$alkyl optionally substituted with OH, $OC_{1-4}$alkyl, SH, or $SC_{1-4}$alkyl.

Specifically, the compounds of the present invention are compounds of formula I wherein $R^1$ is —$NR^4R^5$, —$SO_2R^6$, or —$C_{1-4}$alkyl substituted with —$SR^4$, —S(C=O)$R^4$, —C(=O)$NR^4R^5$, or —$SO_2R^6$; $R^2$ is H or $C_{1-4}$alkyl; and $R^3$ is H or $C_{1-4}$alkyl optionally substituted with OH, $OC_{1-4}$alkyl, SH, or $SC_{1-4}$alkyl.

Specifically, the compounds of the present invention are compounds of formula I wherein $R^1$—$C_{1-4}$alkyl substituted with —$SR^4$, —S(C=O)$R^4$, or —$SO_2R^6$; $R^2$ is H or $C_{1-4}$alkyl; and $R^3$ is H or $C_{1-4}$alkyl.

Specifically, the compounds of the present invention are compounds of formula I wherein $R^1$ a methyl substituted with —SH, or —S(C=O)$CH_3$; $R^2$ is H or $C_{1-4}$alkyl; and $R^3$ is H or $C_{1-4}$alkyl.

Specifically, the compounds of the present invention are compounds of formula I wherein $R^1$ a methyl substituted with —SH, or —S(C=O)$CH_3$; $R^2$ is H or methyl; and $R^3$ is H or methyl.

Examples of the present invention include:
1) (6R,7R)-3-{3-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
2) (6R,7R)-3-{4-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
3) (6R,7R)-3-{5-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
4) (6R,7R)-3-{3-[(acetylsulfanyl)methyl]-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
5) (6R,7R)-3-{3-[(acetylsulfanyl)methyl]-5-(hydroxymethyl)-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
6) (6R,7R)-3-{4-[(acetylsulfanyl)methyl]-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
7) (6R,7R)-3-(3-{[(acetylsulfanyl)acetyl]amino}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
8) (6R,7R)-3-(5-{[(acetylsulfanyl)acetyl]amino}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
9) (6R,7R)-3-(4-{[(acetylsulfanyl)acetyl](propyl)amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
10) (6R,7R)-3-(3-{[(acetylsulfanyl)acetyl](methyl)amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
11) (6R,7R)-7-{[(2Z)-2-(2-amino-1,3-thiazol-4-yl)-2-(methoxyimino)acetyl]amino}-3-(3-{[(methylsulfanyl)acetyl]amino}benzyl)-8-oxo-5-thia-1-azabicyclo[4.2.0]oct-2-ene-2-carboxylic acid;
12) (6R,7R)-3-(3-{[(acetylsulfanyl)acetyl]amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
13) (6R,7R)-7-{[(2Z)-2-(2-amino-1,3-thiazol-4-yl)-2-(methoxyimino)acetyl]amino}-8-oxo-3-{3-[propan-2-yl(sulfanylacetyl)amino]benzyl}-5-thia-1-azabicyclo[4.2.0]oct-2-ene-2-carboxylic acid;
14) (6R,7R)-7-{[(2Z)-2-(2-amino-1,3-thiazol-4-yl)-2-(methoxyimino)acetyl]amino}-3-{2,3-dimethyl-5-[(methylsulfonyl)amino]benzyl}-8-oxo-5-thia-1-azabicyclo[4.2.0]oct-2-ene-2-carboxylic acid;
15) (6R,7R)-7-{[(2Z)-2-(2-amino-1,3-thiazol-4-yl)-2-(methoxyimino)acetyl]amino}-3-{2,4-dimethyl-5-[(methylsulfonyl)amino]benzyl}-8-oxo-5-thia-1-azabicyclo[4.2.0]oct-2-ene-2-carboxylic acid;
16) (6R,7R)-7-{[(2Z)-2-(2-amino-1,3-thiazol-4-yl)-2-(methoxyimino)acetyl]amino}-3-{3-[methyl(methylsulfonyl)amino]benzyl}-8-oxo-5-thia-1-azabicyclo[4.2.0]oct-2-ene-2-carboxylic acid;
17) (6R,7R)-7-{[(2Z)-2-(2-amino-1,3-thiazol-4-yl)-2-(methoxyimino)acetyl]amino}-3-{3-[(methylsulfonyl)amino]benzyl}-8-oxo-5-thia-1-azabicyclo[4.2.0]oct-2-ene-2-carboxylic acid;
18) (6R,7R)-7-{[(2Z)-2-(2-amino-1,3-thiazol-4-yl)-2-(methoxyimino)acetyl]amino}-3-{3-methoxy-5-[(methylsulfonyl)amino]benzyl}-8-oxo-5-thia-1-azabicyclo[4.2.0]oct-2-ene-2-carboxylic acid;
19) (6R,7R)-7-{[(2Z)-2-(2-amino-1,3-thiazol-4-yl)-2-(methoxyimino)acetyl]amino}-3-{3-methyl-5-[(methylsulfonyl)amino]benzyl}-8-oxo-5-thia-1-azabicyclo[4.2.0]oct-2-ene-2-carboxylic acid;
20) (6R,7R)-3-(5-{[2-(acetylsulfanyl)ethyl]sulfamoyl}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
21) (6R,7R)-3-(3-{[2-(acetylsulfanyl)ethyl](ethyl)sulfamoyl}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;
22) (6R,7R)-7-{[(2Z)-2-(2-amino-1,3-thiazol-4-yl)-2-(methoxyimino)acetyl]amino}-3-[2-methoxy-5-(methylsulfamoyl)benzyl]-8-oxo-5-thia-1-azabicyclo[4.2.0]oct-2-ene-2-carboxylic acid;
23) (6R,7R)-7-{[(2Z)-2-(2-amino-1,3-thiazol-4-yl)-2-(methoxyimino)acetyl]amino}-3-[3-(methylsulfamoyl)benzyl]-8-oxo-5-thia-1-azabicyclo[4.2.0]oct-2-ene-2-carboxylic acid;
24) (6R,7R)-7-{[(2Z)-2-(2-amino-1,3-thiazol-4-yl)-2-(methoxyimino)acetyl]amino}-3-[2-methyl-5-(methylsulfamoyl)benzyl]-8-oxo-5-thia-1-azabicyclo[4.2.0]oct-2-ene-2-carboxylic acid;
25) (6R,7R)-7-{[(2Z)-2-(2-amino-1,3-thiazol-4-yl)-2-(methoxyimino)acetyl]amino}-3-[3-(dimethylsulfamoyl)benzyl]-8-oxo-5-thia-1-azabicyclo[4.2.0]oct-2-ene-2-carboxylic acid;
26) (6R,7R)-7-{[(2Z)-2-(2-amino-1,3-thiazol-4-yl)-2-(methoxyimino)acetyl]amino}-3-[3-methoxy-5-(methylsulfamoyl)benzyl]-8-oxo-5-thia-1-azabicyclo[4.2.0]oct-2-ene-2-carboxylic acid;
27) (6R,7R)-7-{[(2Z)-2-(2-amino-1,3-thiazol-4-yl)-2-(methoxyimino)acetyl]amino}-3-[3-methyl-5-(methylsulfamoyl)benzyl]-8-oxo-5-thia-1-azabicyclo[4.2.0]oct-2-ene-2-carboxylic acid; or 28) (6R,7R)-7-{[(2Z)-2-(2-amino-1,3-thiazol-4-yl)-2-(methoxyimino)acetyl]amino}-3-[2-methyl-4-(methylsulfonyl)benzyl]-8-oxo-5-thia-1-azabicyclo[4.2.0]oct-2-ene-2-carboxylic acid;

The following reaction schemes illustrate the general synthetic procedures of the compounds of the present invention. All starting materials are prepared by procedures described in these schemes or by procedures known to one of ordinary skill in the art.

alkyl. A compound of structure (4) could be synthesized using the Stille coupling process by reaction of a suitable stannane (2) with a compound of structure (3) (prepared according the methods described in EP0416410) in the presence of suitable palladium catalyst such as tris(dibenzylidineacetone)dipalladium and an appropriate phosphine ligand such as tris(2-furyl)phosphine at elevated temperatures up to reflux in suitable dipolar aprotic solvents such as THF, 1,4-dioxane or N-methyl-2-pyrrolidone. The protection group can be any Scheme I

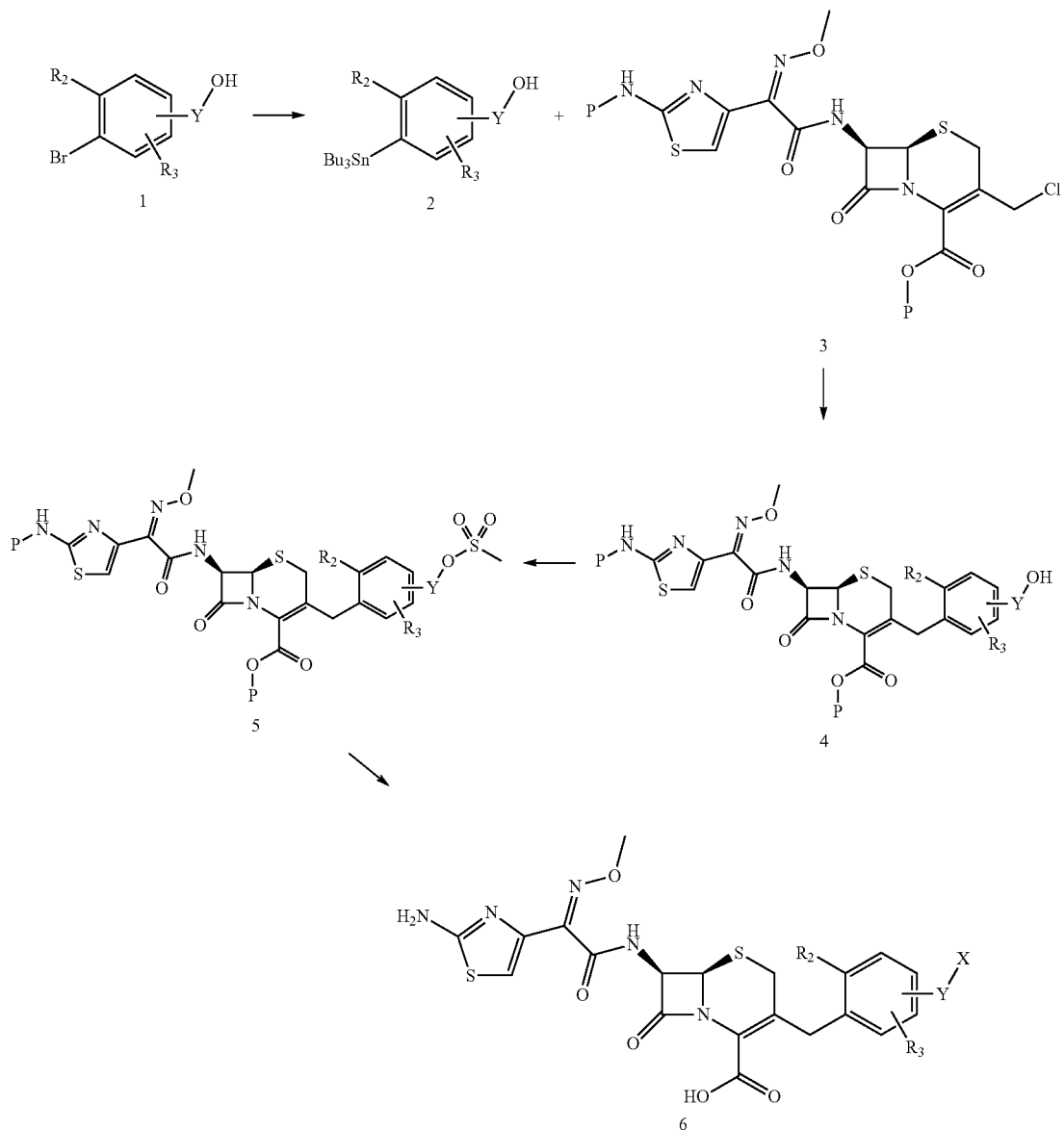

As shown in Scheme I, a compound of structure (2) can be prepared from an arylbromide (1) in a suitable solvent such as tetrahydrofuran (THF), in the presence of a suitable organolithium reagent such as butyllithium and a suitable alkyltinchloride such as tributyltinchloride at temperatures between −78° C. and room temperature for several hours. In the reaction, $R^2$ and $R^3$ are as previously defined. Y is $C_{1-8}$ suitable group such as di-tert-butyl dicarbonate, para-methoxybenzyl ether, para-nitor benzyl ether, or triphenylmethyl.

A compound of structure (5) can be prepared from a compound of structure (4) by addition of a suitable mesylating reagent such as mesyl chloride in the presence of a suitable hindered base such as diisopropylethylamine (DIPEA) or 2,2,6,6-tetramethylpiperidine in a suitable solvent such as dichoromethane (DCM) at temperatures between −78° C. and room temperature for several hours.

A compound of structure (6) may be synthesized from a compound of structure (5) by S-alkylation using a suitable nucleophile followed by removing the protection group P. In this reaction, X is SR⁴ or S(C=O)R⁴. Thus, compounds of structure (5) can reacted with a suitable nucleophile such as thioacetic acid in the presence of a suitable hindered base such as DIPEA or 2,2,6,6-tetramethylpiperidine in an appropriate polar aprotic solvent such a DMF, THF, DMSO or acetonitrile at temperatures between 0° C. and room temperature for several hours. The protection group P can be subsequently removed by the procedures known to one skilled in the art. For example, when the protecting group P is di-tert-butyl dicarbonate or para-methoxybenzyl ether, suitable deprotection conditions involve reaction with an acid such as trifluoroacetic acid in a solvent such as dichloromethane at temperatures between 0° C. and room temperature for several hours.

Scheme II illustrates an alternative method for preparing a compound of the present invention.

with a suitable stannylating reagent such as bistributyltin in the presence of a suitable palladium catalyst such as palladium tetrakistriphenylphosphine in a suitable non-polar solvent such as toluene at temperatures ranging from room temperature to reflux for several hours. Alternatively, the hydrogen on the amine moiety can be further substituted by condensing structure (8) with carboxylic acid derivatives such as commercially available acetylthioglycolic acid in the presence of coupling agents such as O-(7-Azabenzotriazol-1-yl)-N,N,N',N'-tetramethyluronium hexafluorophosphate and a suitable hindered base such as diisopropylethylamine or 2,2,6,6-tetramethylpiperidine in suitable polar aprotic solvents such as DMF or THF at temperatures between 0° C. and reflux for several hours.

Using the Stille coupling process by reaction of a suitable stannane (8) with a compound of structure (3) (can be prepared according to the methods described in EP0416410) in the presence of suitable palladium catalyst such as tris(dibenzylidineacetone)dipalladium and an appropriate phosphine ligand such as tris(2-furyl)phosphine at elevated temperatures up to reflux in a solvent such as THF or 1,4-dioxane, or a dipolar aprotic solvent such as N-methyl-2-pyrrolidone provides a compound of structure (9).

Scheme II

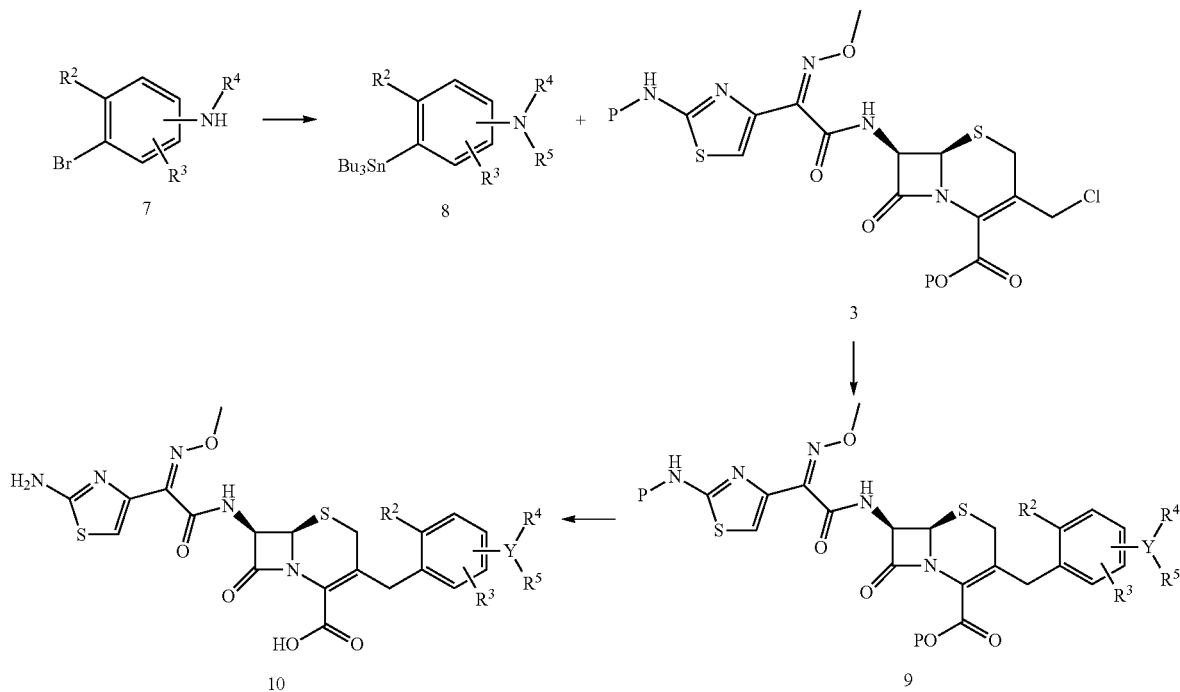

In this reaction, R², R³, R⁴ and R⁵ are as defined previously. P is a suitable protecting group known to one skilled in the art. As shown in Scheme II, a compound of structure (7) may be prepared by N-alkylation a corresponding commercially available phenylamine using a suitable electrophile such as methyliodide or methane sulfonyl chloride in the presence of suitable metal hydride or organolithium bases such as sodium hydride or butyllithium in polar protic solvents such as THF or DMF at temperatures ranging from −78° C. to room temperature.

A compound of structure (8) wherein R⁴ is hydrogen may be prepared from a compound of structure (7) by reaction A compound of structure (10) of the present invention may be prepared from compounds of formula (9) wherein P is a suitable protecting group by deprotection procedures known to one skilled in the art. For example, when the protecting group P is di-tert-butyl dicarbonate, para-methoxybenzyl ether, para-nitor benzyl ether, or triphenylmethyl suitable deprotection conditions involve reaction with an acid such as trifluoroacetic acid in a solvent such as dichloromethane at temperatures between 0° C. and room temperature for several hours.

Scheme III illustrates another alternative method for preparing a compound of the present invention.

Scheme III

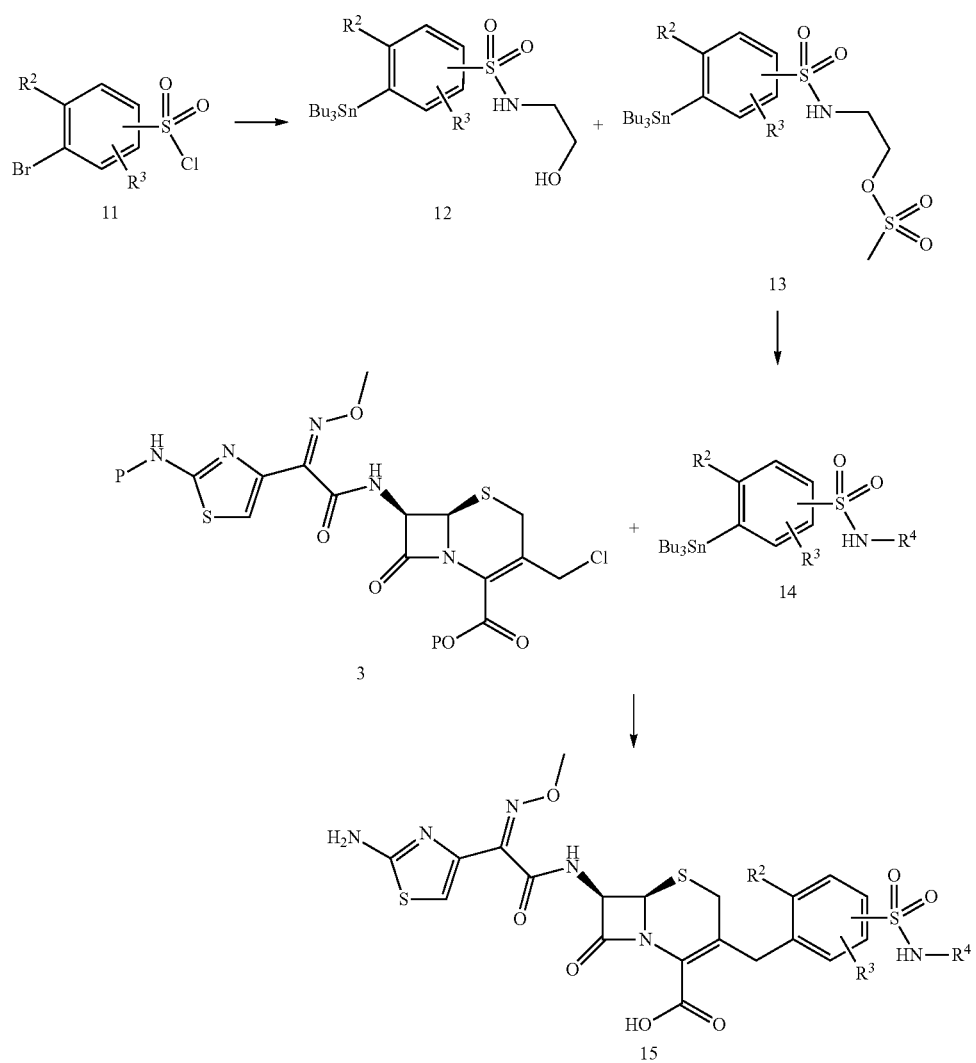

As shown in Scheme III, a compound of structure (12) may be prepared by reaction of a commercially available compound (II) with a suitable amine derivative such as ethanolamine in a suitable polar aprotic solvent such as THF or DMSO at temperatures ranging from −78° C. to reflux for several hours. The resultant sulfonamide then reacts with a suitable stannylating reagent such as bistributyltin in the presence of a suitable palladium catalyst such as palladium tetrakistriphenylphosphine in a suitable non-polar solvent such as toluene at temperatures ranging from room temperature to reflux for several hours. Subsequently, addition of a suitable mesylating reagent such as mesyl chloride in the presence of a suitable hindered base such as diisopropylethylamine (DIPEA) or 2,2,6,6-tetramethylpiperidine in a suitable solvent such as dichoromethane (DCM) at temperatures between −78° C. and room temperature for several hours provides the methane sulfonyl compound (13).

A compound of structure (14) may be prepared from a compound of structure (13) by S-alkylation using a suitable nucleophile. Thus, compounds of structure (14) can be reacted with a suitable nucleophile such as thioacetic acid in the presence of a suitable hindered base such as DIPEA or 2,2,6,6-tetramethylpiperidine in an appropriate polar aprotic solvent such a DMF, THF, DMSO or acetonitrile at temperatures between 0° C. and room temperature for several hours. Following the procedure described in Scheme II by using the Stille coupling process and deprotection condition provides a compound of the present invention (15).

Additionally, many of the compounds have reactive functional groups that generally need to be derivatized with a protecting group in order to avoid unwanted side reactions. For example, functional groups such as alcohols, acid groups, and amines generally are protected while a reaction is carried out at a different site in the molecule, and then the protecting group is subsequently removed following the desired chemical transformation. The use of such protecting groups may follow the standard methods in organic chemistry synthesis, as described, for example, in T. W. Green and P. G. Wuts, *Protective Groups in Organic Synthesis*, $2^{nd}$ edition, New York City: John Wiley & Sons, 1991. Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl. vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by acidolysis or hydrogenolysis, TBDMS by treatment with fluoride ions, and TCEC by treatment with zinc.

Pharmaceutical Salts

The compound of formula I may be used in its native form or as a salt. In cases where forming a stable nontoxic acid or base salt is desired, administration of the compound as a pharmaceutically acceptable salt may be appropriate. Pharmaceutically acceptable salts of the compounds of formula I include the acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences", Mack Pub. Co., New Jersey (1991).

The formulations of the invention can be designed to be short-acting, fast-releasing, long-acting, extended-releasing, or controlled-releasing. Specifically, the formulation of the invention can be an extended release form. Thus, the pharmaceutical formulations can also be formulated for controlled release or for slow release.

Dosage

Pharmaceutical compositions suitable for use in the present invention include compositions wherein the active ingredients are contained in an amount sufficient to achieve the intended purpose, i.e., control or the treatment of infections. More specifically, a therapeutically effective amount means an amount of compound effective to prevent, alleviate or ameliorate symptoms/signs of infections or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.1 mg to about 20 mg/kg of body weight/day, preferably about 0.1 to about 5 mg/kg of body weight/day. It is to be understood that the dosages may vary depending upon the requirements of each subject and the severity of the infections.

The desired dose may conveniently be presented in a single dose or as divided doses administered at appropriate intervals, for example, as two, three, four or more sub-doses per day. Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Medical and Veterinary Uses

Compounds of the present invention provides novel cephalosporin antibacterial agents for the treatment of bovine respiratory disease infections in cattle caused by Gram-negative respiratory pathogens such as *Mannheimia haemolytica* (*M. haem.*), *Pasteurella multocida* (*P. multo*), and *Histophilus somni* with low relative antibacterial activity against zoonotic pathogens such as *Escherichia coli* (*E. coli.*) *Salmonella* and *Campylobacter*.

Antibacterial Assays

Compounds of the present invention were tested against an assortment of Gram-negative and Gram-positive organisms using the industrial standard techniques described in *Methods for Dilution Antimicrobial Susceptibility Tests for Bacteria That grow Aerobically; Approved Standard—Eighth Edition, M07-A8, Vol. 29 No. 2 Replaces M07-A7 Vol. 26 No. 2.* The results of the evaluation are shown in Tables I. The data demonstrates very good antibacterial activity against BRD pathogens *M. haem.* and *P. multo*, and minimized activity against *E. coli*. The fifth column shows the *E. coli* selectivity margin over *P. multo*. When comparing the activity against these isolates with that of the marketed human health drug of cefepime (screened in the same panel), the exemplified compounds of the present invention show >200 times more selectivity over *E. coli*.

| Examples | E. coli 25922 (ug/mL) | M. haemo 43411 (ug/mL) | P. multo 43719 (ug/mL) | E. coli/ P. multocida |
|---|---|---|---|---|
| 1 | 16 | 0.06 | 0.03 | 533 |
| 2 | 32 | 0.25 | 0.06 | 533 |
| 3 | 32 | 0.25 | 0.125 | 256 |
| 4 | 32 | 0.5 | 0.25 | 128 |
| 5 | 32 | 0.125 | 0.06 | 533 |
| 6 | 32 | 0.5 | 0.25 | 128 |
| 7 | 16 | 0.06 | 0.06 | 266 |
| 8 | 16 | 0.06 | 0.06 | 266 |
| 9 | 64 | 0.5 | 0.25 | 256 |
| 10 | 32 | 0.125 | 0.06 | 533 |
| 11 | 4 | 0.03 | 0.03 | 133 |
| 12 | 8 | 0.03 | 0.06 | 133 |
| 13 | 8 | 0.06 | 0.03 | 266 |
| 14 | 16 | 0.06 | 0.03 | 533 |
| 15 | 32 | 0.5 | 0.125 | 256 |
| 16 | 16 | 0.03 | 0.03 | 533 |
| 17 | 8 | 0.015 | 0.03 | 266 |
| 18 | 16 | 0.08 | 0.06 | 266 |
| 19 | 8 | 8 | 0.008 | 1000 |
| 20 | 64 | 0.25 | 0.25 | 256 |

-continued

| Examples | E. coli 25922 (ug/mL) | M. haemo 43411 (ug/mL) | P. multo 43719 (ug/mL) | E. coli/ P. multocida |
|---|---|---|---|---|
| 21 | 32 | 0.125 | 0.03 | 1066 |
| 22 | 64 | 0.125 | 0.25 | 256 |
| 23 | 16 | 0.06 | 0.125 | 128 |
| 24 | 4 | 0.008 | 0.015 | 266 |
| 25 | 8 | 0.008 | 0.008 | 1000 |
| 26 | 4 | 0.008 | 0.015 | 266 |
| 27 | 8 | 0.008 | 0.015 | 533 |
| 28 | 4 | 0.06 | 0.03 | 133 |

The synthesis of compounds of the present invention is further illustrated by the following examples. The starting materials and various intermediates utilized in the examples may be obtained from commercial sources, or are readily prepared from commercially available organic compounds, using well-known methods to one skilled in the art.

EXAMPLES

Example 1

Preparation of (6R,7R)-3-{3-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

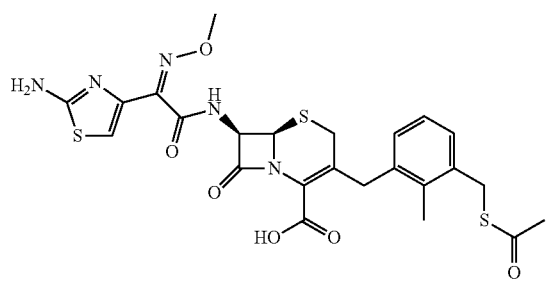 [SMILES: CO/N=C(\C(=O)N[C@@H]1C(=O)N2C(C(=O)O)=C(Cc3cccc(CSC(C)=O)c3C)CS[C@H]12)c1csc(N)n1]

Step 1 Preparation of [2-methyl-3-(tributylstannanyl)phenyl]methanol

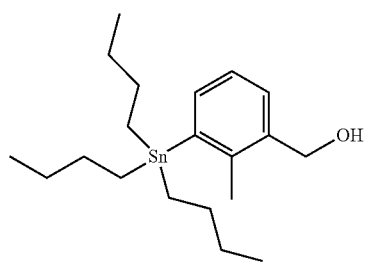 [SMILES: CCC[CH2][Sn]([CH2]CCC)([CH2]CCC)[c]1cccc(CO)c1C]

Butyl lithium (65.5 mL, 164 mmol) is added dropwise to a solution of (3-bromo-2-methylphenyl)methanol (15.0 g, 76.6 mmol) in THF (165 mL) at −78° C. After 1 hour at −78° C. tributyltinchloride (45.0 mL, 164 mmol) is added and the mixture brought to room temperature over a period of 3 hours then stirred for 12 hours. Saturated ammonium chloride (100 mL), followed by water (100 mL) is added at 0° C. After allowing warming to room temperature the mixture is extracted with diethylether (3×100 mL). The combined extracts are dried over magnesium sulfate, filtered and the solvent removed under reduced pressure to give the title compound as an oil, which is purified by column chromatography eluting from neat heptane to 30% ethylacetate/heptane (20.5 g): $^1$H NMR (CDCl$_3$): 7.37-7.31 (2H), 7.20-7.17 (1H), 4.72 (2H), 2.42 (3H), 1.57-1.50 (6H), 1.39-1.31 (6H), 1.11-1.07 (6H), 0.90 (9H).

Step 2 Preparation of 4-methoxybenzyl (6R,7R)-7-{[(2Z)-2-{2-[(tert-butoxycarbonyl)amino]-1,3-thiazol-4-yl}-2-(methoxyimino)acetyl]amino}-3-[3-(hydroxymethyl)-2-methylbenzyl]-8-oxo-5-thia-1-azabicyclo[4.2.0]oct-2-ene-2-carboxylate

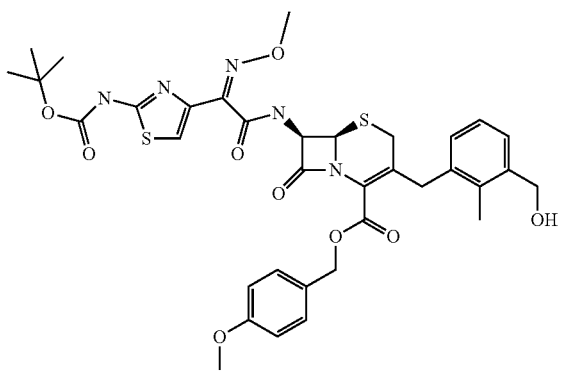 [SMILES: CO/N=C(\C(=O)N[C@@H]1C(=O)N2C(C(=O)OCc3ccc(OC)cc3)=C(Cc3cccc(CO)c3C)CS[C@H]12)c1csc(NC(=O)OC(C)(C)C)n1]

Tris(2-furyl)phosphine (352 mg, 1.50 mmol) is added to 4-methoxybenzyl (6R,7R)-7-{[(2Z)-2-{2-[(tert-butoxycarbonyl)amino]-1,3-thiazol-4-yl}-2-(methoxyimino)acetyl]amino}-3-(chloromethyl)-8-oxo-5-thia-1-azabicyclo[4.2.0]oct-2-ene-2-carboxylate (described in EP0416410, 5.00 g, 7.67 mmol) in dioxane (75 mL), followed by tris(dibenzylidineacetone)dipalladium (693 mg, 0.75 mmol) then [2-methyl-3-(tributylstannanyl)phenyl]methanol (3.70 g, 8.99 mmol, Step 1) and the mixture heated to 75° C. for 24 hours. After allowing to cool to room temperature, the solvent is removed under reduced pressure to give the title compound. The crude material is purified using column chromatography eluting from 30% ethylacetate/heptane to neat ethylacetate to give a solid (3.16 g); m/z (CI) 738 [M+H]$^+$.

Step 3 Preparation of 4-methoxybenzyl (6R,7R)-7-{[(2Z)-2-{2-[(tert-butoxycarbonyl)amino]-1,3-thiazol-4-yl}-2-(methoxyimino)acetyl]amino}-3-(2-methyl-3-{[(methylsulfonyl)oxy]methyl}benzyl)-8-oxo-5-thia-1-azabicyclo[4.2.0]oct-2-ene-2-carboxylate

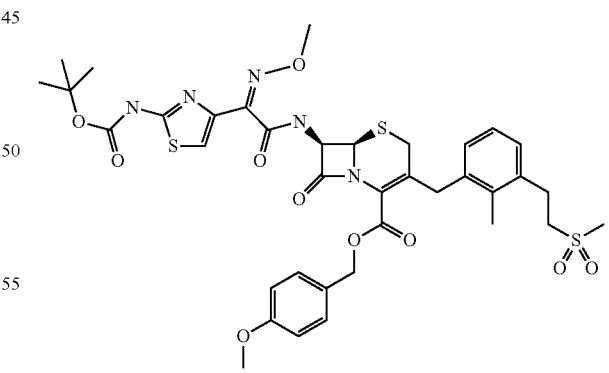

Methanesulfonyl chloride (0.40 mL, 5.10 mmol) followed by DIPEA (1.18 mL, 6.78 mmol) is added to an ice cold solution of the product of Step 2 (2.50 g, 3.39 mmol) in DCM (26.1 mL). After stirring at 0° C. for 16 hours, the mixture is diluted with ethylacetate (30 mL), washed with water, dried over magnesium sulfate, filtered and the solvent removed under reduced pressure to give the title compound as a solid (2.76 g) which is used in the next step without further purification. m/z (CI) 816 [M+H]$^+$.

Step 4 Preparation of 4-methoxybenzyl (6R,7R)-3-{3-[(acetylsulfanyl)methyl]-2-methylbenzyl}-7-{[(2Z)-2-{2-[(tert-butoxycarbonyl)amino]-1,3-thiazol-4-yl}-2-(methoxyimino)acetyl]amino}-8-oxo-5-thia-1-azabicyclo[4.2.0]oct-2-ene-2-carboxylate

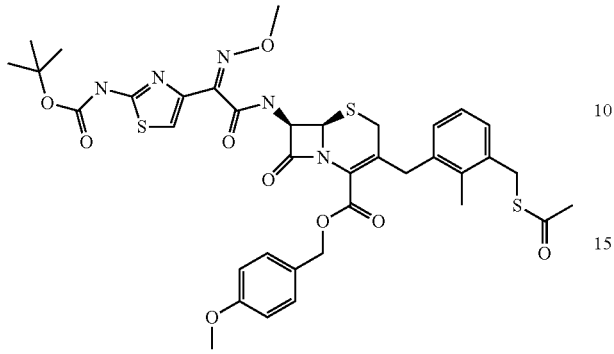

Thioacetic acid (0.47 mL, 6.37 mmol) followed by DIPEA (0.56 mL, 3.19 mmol) is added to a solution of the product of Step 3 (2.6 g, 3.2 mmol) in DMF (20 mL) at 0° C. After stirring for 1.5 hours ethylacetate is added. The mixture is washed with water, dried over magnesium sulfate, filtered and the solvent removed under reduced pressure to give the title compound as a residue, which is further purified using column chromatography eluting from neat heptane to neat EtOAc to give a solid: (2.3 g); m/z (CI) 796 [M+H]$^+$.

Step 5 Preparation of (6R,7R)-3-{3-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid TFA (10 mL) is added to a solution of the product of Step 4 (2.00 g, 2.51 mmol) in DCM (20 mL). After 3 hours, the reaction mixture is diluted with toluene (10 mL), the solvent is removed under reduced pressure and the resultant oil purified using reverse phase column chromatography eluting from neat water to neat MeCN to give the title compound as a pale yellow solid (750 mg). $^1$HNMR (DMSO-d$_6$): 9.65 (1H), 7.20-6.97 (3H), 6.78 (1H), 5.76-5.70 (1H), 5.18 (1H), 4.15 (2H), 3.85 (3H), 3.80 (2H). 3.37 (1H), 3.15 (1H), 2.34 (3H), 2.16 (3H). m/z (CI) 576 [M+1]$^+$.

Example 2

Preparation of (6R,7R)-3-{4-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

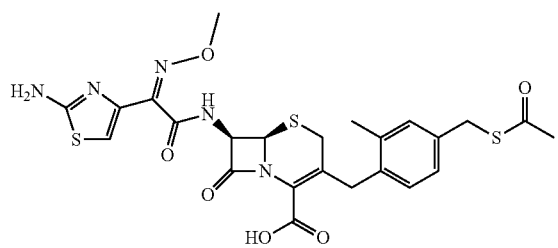 [SMILES: CO/N=C(\C(=O)N[C@@H]1C(=O)N2C(C(=O)O)=C(Cc3ccc(CSC(C)=O)cc3C)CS[C@H]12)c1csc(N)n1]

Following the general procedure of Example 1, Steps 1-5, and making non-critical variations but using commercially available (4-bromo-3-methylphenyl)methanol as an intermediate, the title compound is obtained. (31 mg) $^1$HNMR (DMSO-d$_6$): 9.56 (1H), 6.94-7.01 (3H), 6.71 (1H), 5.65 (1H), 5.11 (1H), 3.97 (2H), 3.78 (3H), 3.66 (2H), 3.29 (1H), 3.09 (1H), 2.27 (3H), 2.13 (3H). m/z (CI) 576 [M+H]$^+$.

Example 3

Preparation of (6R,7R)-3-{5-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

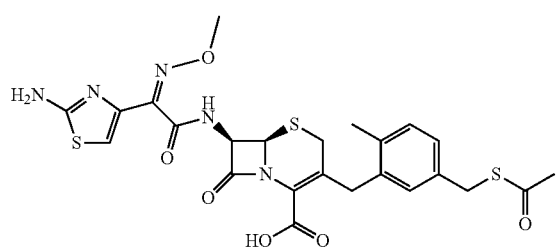 [SMILES: CO/N=C(\C(=O)N[C@@H]1C(=O)N2C(C(=O)O)=C(Cc3cc(CSC(C)=O)ccc3C)CS[C@H]12)c1csc(N)n1]

Following the general procedure of Example 1, Steps 1-5, and making non-critical variations but using commercially available 3-Bromo-4-methylbenzyl alcohol as an intermediate, the title compound is obtained. $^1$HNMR (DMSO-d$_6$): 9.63 (1H), 7.06 (3H), 6.79 (1H), 5.71 (1H), 5.17 (1H), 4.03 (2H), 3.85-4.03 (4H), 3.70 (1H), 3.23 (2H), 2.33 (3H), 2.19 (3H). m/z (CI) 576 [M+H]$^+$.

Example 4

Preparation of (6R,7R)-3-{3-[(acetylsulfanyl)methyl]-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

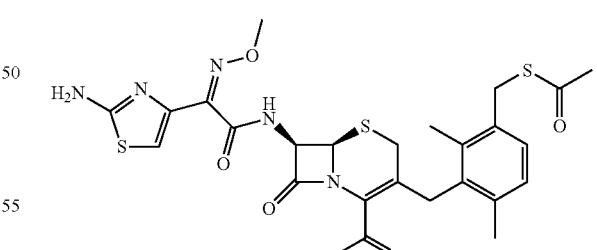

Following the general procedure of Example 1, Steps 1-5, and making non-critical variations but using (3-bromo-2,4-dimethylphenyl)methanol (described in WO10129379) as an intermediate, the title compound is obtained. $^1$HNMR (DMSO-d$_6$): 9.57 (1H), 7.12 (1H), 6.99 (1H), 6.77 (1H), 5.69 (1H), 5.12 (1H), 4.13 (2H), 4.07 (2H), 3.96 (2H), 3.84 (3H), 2.93 (2H), 2.35 (3H), 2.24 (3H), 2.18 (3H). m/z (CI) 590 [M+H]$^+$.

Example 5

Preparation of (6R,7R)-3-{3-[(acetylsulfanyl)methyl]-5-(hydroxymethyl)-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

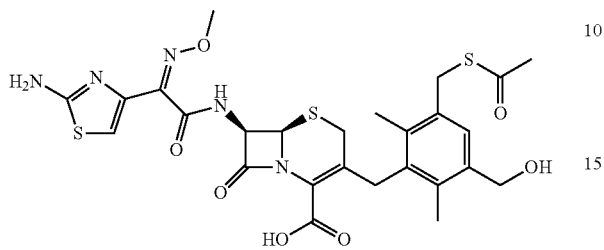

Following the general procedure of Example 1—Steps 2-5, and making non-critical variations but using the product of Step 3, Example 5 as an intermediate, the title compound is obtained. ¹HNMR (DMSO-d$_6$): 9.57 (1H), 7.22 (1H), 6.77 (1H), 5.66 (1H), 5.11 (1H), 4.43 (2H), 4.13 (3H), 3.96 (1H), 2.89 (2H), 2.34 (3H), 2.16 (3H), 2.13 (3H). m/z (CI) 620 [M+H]$^+$.

Step 1 Preparation of (5-bromo-4,6-dimethylbenzene-1,3-diyl)dimethanediyl diacetate

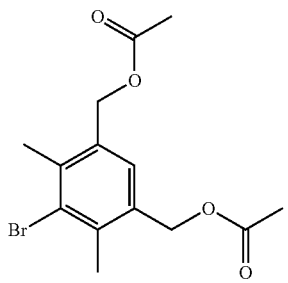 [SMILES: CC(=O)OCc1cc(COC(C)=O)c(C)c(Br)c1C]

Sodium acetate (33.6 g, 389 mmol) is added to a solution of 3-bromo-1,5-bis(chloromethyl)-2,4-dimethylbenzene (described in WO08151288, 54.8 g, 194 mmol) in DMF (120 mL) and the mixture heated to 80° C. for 16 hours. The mixture is cooled to room temperature and water (100 mL) added. The slurry is filtered, washed with water (200 mL) and dried in a vacuum over at 45° C. for 48 hours to give a solid (61.4 g).): ¹HNMR (DMSO-d$_6$): 7.31 (1H), 5.11 (4H), 2.37 (6H), 2.05 (6H).

Step 2 Preparation of (5-bromo-4,6-dimethylbenzene-1,3-diyl)dimethanol

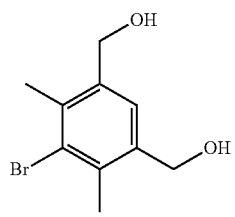

Potassium hydroxide (24.1 g, 429 mmol) is added to a mixture of (5-bromo-4,6-dimethylbenzene-1,3-diyl)dimethanediyl diacetate (61.4 g, 186.4 mmol) in methanol (300 mL) and the mixture heated to 50° C. for 1 hour. The solvent is removed under reduced pressure and the solid diluted with water (600 mL) and 3N hydrochloric acid (175 mL). The mixture is stirred for 10 minutes and the precipitate filtered and dried in a vacuum oven overnight to give a solid (42.9 g).): ¹HNMR (DMSO-d$_6$): 7.35 (1H), 5.15 (2H), 4.50 (4H), 2.35 (6H).

Step 3 Preparation of [3-bromo-5-({[tert-butyl(dimethyl)silyl]oxy}methyl)-2,4-dimethylphenyl]methanol

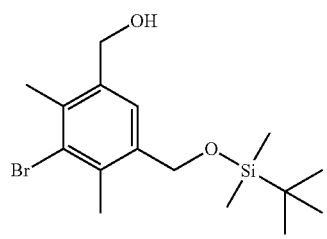 [SMILES: Cc1c(CO)cc(CO[Si](C)(C)C(C)(C)C)c(C)c1Br]

tert-Butyldimethylsilyl chloride (6.15 g, 408.8 mmol), imidazole (3.15 g, 44.9 mmol) and DMAP (0.05 g, 0.41 mmol) are added to a solution of (5-bromo-4,6-dimethylbenzene-1,3-diyl)dimethanol (10.0 g, 41 mmol) at room temperature and the mixture stirred for 16 hours. The mixture is diluted with water (400 mL) and extracted with ethylacetate (1400 mL). The organics are washed with 1N hydrochloric acid (200 mL), saturated sodium hydrogen carbonate (200 mL) and dried over sodium sulfate and the solvent removed under reduced pressure to give a wet solid. The solid is diluted with heptane (50 mL), filtered and washed with heptane (10 mL) to give a white solid (3.75 g). ¹HNMR (DMSO-d$_6$): 7.30 (1H), 5.05 (1H), 4.62 (2H), 4.40 (2H), 2.22 (6H), 0.82 (9H), 0.10 (6H).

Example 6

Preparation of (6R,7R)-3-{4-[(acetylsulfanyl)methyl]-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

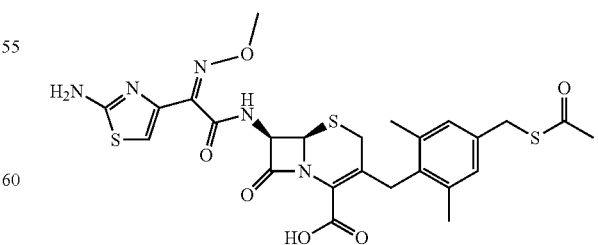

Following the general procedure of Example 1, Steps 1-5, and making non-critical variations but using commercially available (4-bromo-3,5-dimethylphenyl)methanol as an intermediate, the title compound is obtained. ¹HNMR (DMSO-d₆): 9.58 (1H), 6.94 (2H), 6.78 (1H), 5.66 (1H), 5.11 (1H), 4.02 (2H), 3.92 (2H), 3.84 (3H), 2.95 (2H), 2.35 (3H), 2.21 (6H). m/z (CI) 590 [M+H]⁺.

Example 7

Preparation of (6R,7R)-3-(3-{[(acetylsulfanyl)acetyl]amino}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxyl is acid

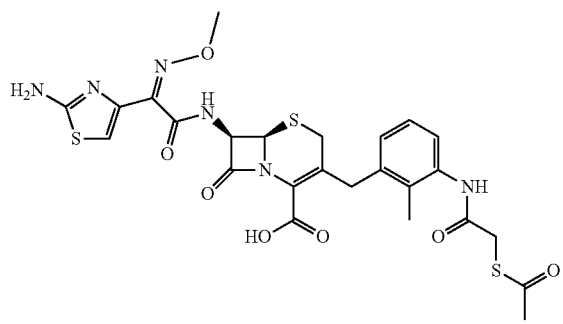 [SMILES: CO/N=C(\C(=O)N[C@@H]1C(=O)N2C(C(=O)O)=C(Cc3cccc(NC(=O)CSC(C)=O)c3C)CS[C@H]12)c1csc(N)n1]

Following the general procedure of Example 1, Steps 2 and 5, and making non-critical variations but using the product of Step 2, Example 7 as an intermediate, the title compound is obtained. (58 mg) ¹HNMR (DMSO-d₆) 9.60 (1H), 9.56 (1H), 7.10 (1H), 7.04 (1H), 6.90 (1H), 6.74 (1H), 5.67 (1H), 5.12 (1H), 3.79 (3H), 3.77 (2H), 3.74 (1H), 3.32 (1H), 3.10 (1H), 2.32 (3H), 2.02 (3H). m/z (CI) 618.7 [M+H]⁺.

Step 1 Preparation of 2-methyl-3-(tributylstannanyl)aniline

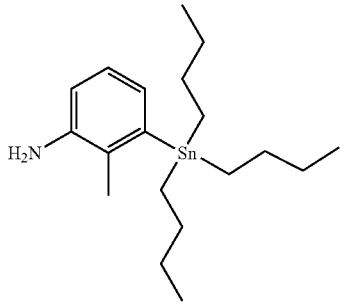 [SMILES: CCC[CH2][Sn]([CH2]CCC)([CH2]CCC)[c]1cccc(N)c1C]

2-amino-6-bromotoluene (commercially available, 1.00 g, 5.38 mmol), bistributyltin (3.86 g, 6.45 mmol) and palladium tetrakistriphenylphosphine (0.62 g, 0.54 mmol) were mixed together in a microwave reaction vial and heated at 120° C. for 8 hours. The solvent was removed under reduced pressure and the resultant black oil purified using column chromatography eluting from neat heptane to neat EtOAc to give the titled compound as a clear oil: (2.51 g) m/z (CI) 396 [M+H]⁺.

Step 2 Preparation of S-(2-{[2-methyl-3-(tributylstannanyl)phenyl]amino}-2-oxoethyl)ethanethioate

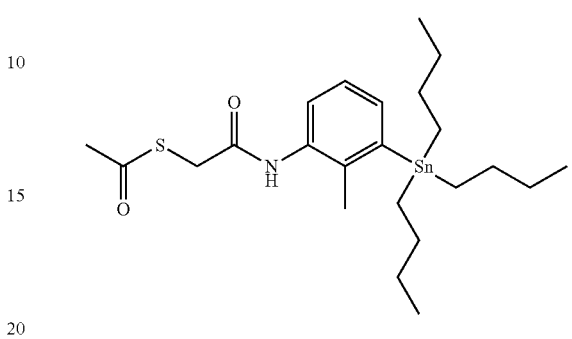

O-(7-Azabenzotriazol-1-yl)-N,N,N',N'-tetramethyluronium hexafluorophosphate (3.20 g, 8.24 mmol) followed by DIPEA (2.43 mL, 13.9 mmol) is added to a solution of 2-methyl-3-(tributylstannanyl)aniline (2.51 g, 6.34 mmol) and commercially available acetylthioglycolic acid (0.94 g, 6.97 mmol) in THF (31.7 mL) at 0° C. and the reaction mixture is stirred for 2 hours. The mixture is diluted with ethylacetate, washed twice with sat. NaHCO₃, then brine, dried over magnesium sulfate, filtered and evaporated. The crude product is further purified using column chromatography eluting from neat heptane to neat EtOAc to give an oily residue: (2.49 g) m/z (CI) 512.1 [M+H]⁺.

Example 8

Preparation of (6R,7R)-3-(5-{[(acetylsulfanyl)acetyl]amino}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxyl is acid

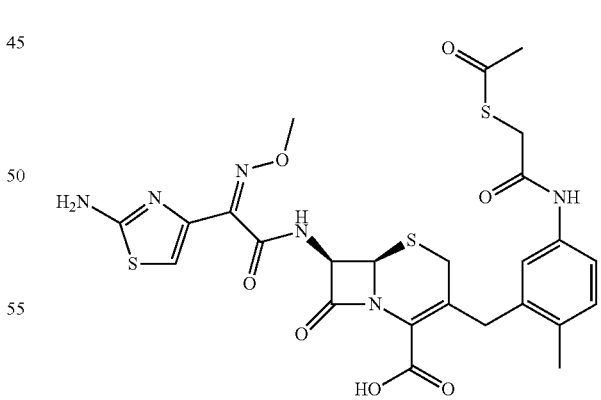

Following the general procedure of Example 7, and making non-critical variations but using the product of commercially available 3-bromo-4-methylaniline as an starting material, the title compound is obtained. ¹HNMR (DMSO-d₆): 10.15 (1H), 9.64 (1H), 7.42 (1H), 7.27 (1H), 7.08 (1H), 6.79 (1H), 5.73-5.70 (1H), 5.14 (1H), 3.90-3.72 (7H). 3.32 (1H), 3.16 (1H), 2.37 (3H), 2.19 (3H). m/z (CI) 619 [M+1]⁺.

Example 9

Preparation of (6R,7R)-3-(4-{[(acetylsulfanyl)acetyl]propyl)amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

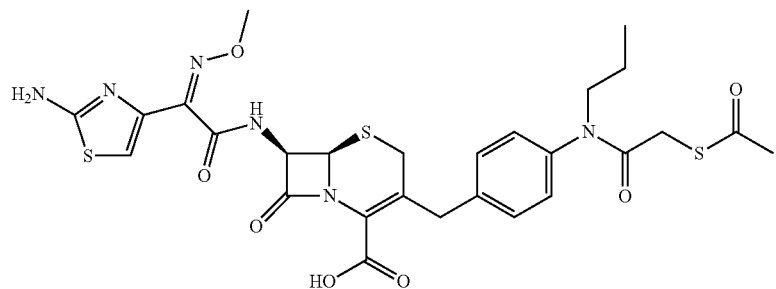

Following the general procedure of Example 7, and making non-critical variations but using commercially available 4-bromo-N-propylbenzenamine, the title compound is obtained. $^1$HNMR (DMSO-d$_6$): 9.62 (1H), 8.13 (1H), 7.37 (2H), 7.32 (2H), 7.16 (1H), 6.76 (1H), 6.73 (1H), 5.74 (1H), 5.20 (1H), 3.99 (1H), 3.83 (3H), 3.48-3.60 (3H), 3.21 (1H), 2.27 (3H), 1.39 (2H), 0.81 (3H). m/z (CI) 647 [M+H]$^+$.

Example 10

Preparation of (6R,7R)-3-(3-{[(acetylsulfanyl)acetyl]methyl)amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

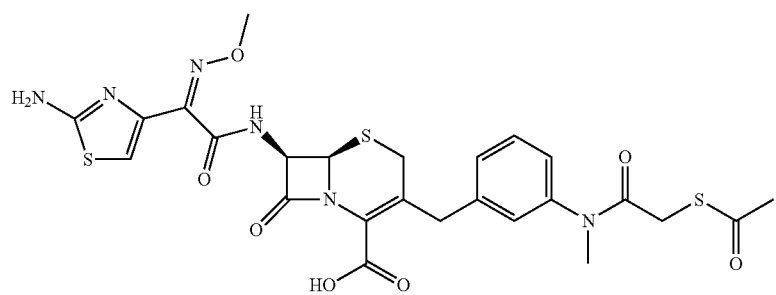

Following the general procedure of Example 7, and making non-critical variations but using commercially available 3-bromo-N-methylaniline, the title compound is obtained. $^1$HNMR (DMSO-d$_6$): 9.55 (1H), 7.37 (1H), 7.18-7.26 (3H), 6.70 (1H), 5.67 (1H), 5.12 (1H), 3.87 (1H), 3.77 (3H), 3.63 (1H), 3.47 (1H), 3.10-3.20 (3H), 2.22 (3H). m/z (CI) 619 [M+H]$^+$.

Example 11

Preparation of (6R,7R)-7-{[(2Z)-2-(2-amino-1,3-thiazol-4-yl)-2-(methoxyimino)acetyl]amino}-3-(3-{[(methylsulfanyl)acetyl]amino}benzyl)-8-oxo-5-thia-1-azabicyclo[4.2.0]oct-2-ene-2-carboxylic acid

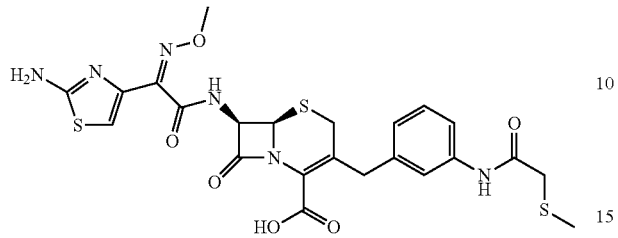

Following the general procedure of Example 7, and making non-critical variations but using 3-(tributylstannanyl) aniline (described in WO8907097) and commercially available (Methylthio)acetic acid, the title compound is obtained. $^1$HNMR (DMSO-d$_6$): 10.05 (1H), 9.61 (1H), 7.54 (1H), 7.45 (1H), 7.25 (1H), 6.98 (1H), 6.77 (1H), 5.72 (1H), 5.17 (1H), 3.94 (1H), 3.84 (3H), 3.57 (1H), 3.48 (1H), 3.25 (2H), 3.20 (1H), 2.16 (3H). m/z (CI) 577 [M+H]$^+$.

Example 12

Preparation of (6R,7R)-3-(3-{[(acetylsulfanyl)acetyl]amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

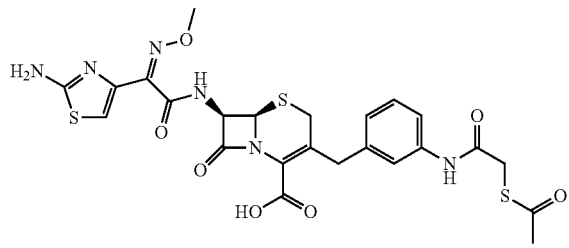 [SMILES: CO/N=C(\C(=O)N[C@@H]1C(=O)N2C(C(=O)O)=C(Cc3cccc(NC(=O)CSC(C)=O)c3)CS[C@H]12)c1csc(N)n1]

Following the general procedure of Example 7, and making non-critical variations but using 3-(tributylstannanyl) aniline (described in WO07124435) and commercially available acetylthioglycolic acid, the title compound is obtained. $^1$HNMR (DMSO-d$_6$): 10.05 (1H), 9.61 (1H), 7.54 (1H), 7.45 (1H), 7.25 (1H), 6.98 (1H), 6.77 (1H), 5.72 (1H), 5.17 (1H), 3.94 (1H), 3.84 (3H), 3.57 (1H), 3.48 (1H), 3.25 (2H), 3.20 (1H), 2.16 (3H). m/z (CI) 577 [M+H]$^+$.

Example 13

Preparation of (6R,7R)-7-{[(2Z)-2-(2-amino-1,3-thiazol-4-yl)-2-(methoxyimino)acetyl]amino}-8-oxo-3-{3-[propan-2-yl(sulfanylacetyl)amino]benzyl}-5-thia-1-azabicyclo[4.2.0]oct-2-ene-2-carboxylic acid

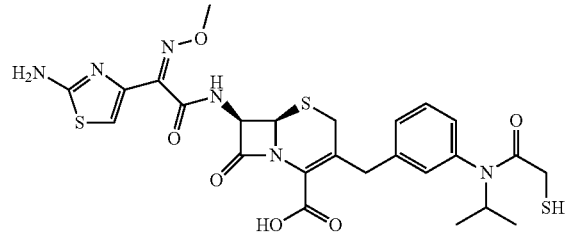 [SMILES: CO/N=C(\C(=O)N[C@@H]1C(=O)N2C(C(=O)O)=C(Cc3cccc(N(C(=O)CS)C(C)C)c3)CS[C@H]12)c1csc(N)n1]

Following the general procedure of Example 1, Steps 2 and 5, and making non-critical variations but using the product of Step 2, Example 13 as an intermediate, the title compound is obtained. $^1$HNMR (DMSO-d$_6$): 10.07 (1H), 9.60 (1H), 7.51 (1H), 7.45 (1H), 7.25 (1H), 6.98 (1H), 6.76 (1H), 5.73 (1H), 5.16 (1H), 3.97 (1H), 3.81-3.85 (4H), 3.56 (1H), 3.47 (1H), 3.32 (2H), 3.08 (1H), 1.23 (6H). m/z (CI) 605 [M+H]$^+$.

Step 1 Preparation of S-(2-oxo-2-{[3-(tributylstannanyl)phenyl]amino}ethyl)ethanethioate

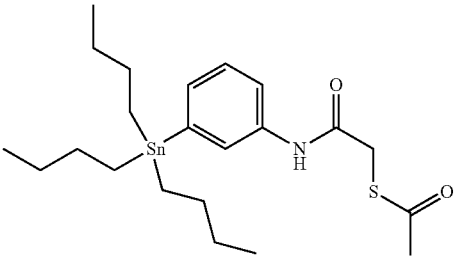 [SMILES: CCC[CH2][Sn]([CH2]CCC)([CH2]CCC)[c]1cccc(NC(=O)CSC(C)=O)c1]

Following the general procedure of Example 7, Step 2, and making non-critical variations but using 3-(tributylstannanyl) aniline (described in WO07124435) and commercially available acetylthioglycolic acid, the title compound is obtained: (1.03 g) m/z (CI) 498 [M+H]$^+$.

Step 2 Preparation of N-(propan-2-yl)-2-sulfanyl-N-[3-(tributylstannanyl)phenyl]acetamide

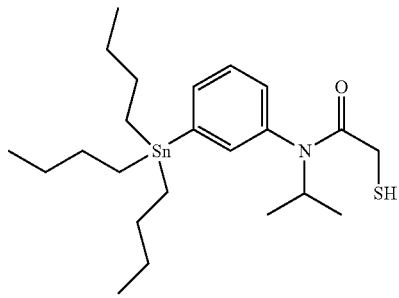 [SMILES: CCC[CH2][Sn]([CH2]CCC)([CH2]CCC)[c]1cccc(N(C(=O)CS)C(C)C)c1]

Sodium hydroxide (60 mg, 1.50 mmol) is added to a mixture of the product of Step 1 (500 mg, 1.00 mmol) and isopropyl bromide (113 μL, 1.20 mmol) in DMF (1 mL). After stirring at room temperature overnight, the mixture is partitioned between brine and ethylacetate. The organic layer is separated, dried over magnesium sulfate and the solvent removed under reduced pressure to give an oil. The crude product is further purified using column chromatography eluting from neat heptane to neat EtOAc to give the title compound as an oily residue (150 mg); m/z (CI) 498 [M+H]$^+$.

Example 14

Preparation of (6R,7R)-7-{[(2Z)-2-(2-amino-1,3-thiazol-4-yl)-2-(methoxyimino)acetyl]amino}-3-{2,3-dimethyl-5-[(methylsulfonyl)amino]benzyl}-8-oxo-5-thia-1-azabicyclo[4.2.0]oct-2-ene-2-carboxylic acid

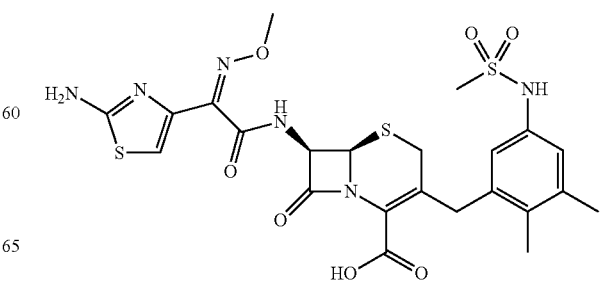

Following the general procedure of Example 1, Steps 2 and 5, and making non-critical variations but using the product of Step 2, Example 14 as an intermediate, the title compound is obtained: (50 mg): $^1$HNMR (DMSO-$d_6$): 9.59 (1H), 9.43 (1H), 6.91-6.93 (2H), 6.76 (1H), 5.70 (1H), 5.13 (1H), 3.94 (1H), 3.84 (3H), 3.74 (1H), 3.28 (1H), 3.18 (1H), 2.92 (3H), 2.22 (3H), 2.08 (3H). m/z (CI) 595 [M+H]$^+$.

Step 1 Preparation of N-(3-bromo-4,5-dimethylphenyl)methanesulfonamide

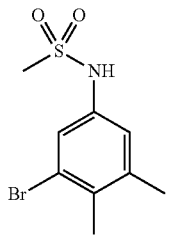

Methanesulfonyl chloride (1.15 mL, 15.0 mmol) is added to 3-bromo-4,5-dimethylaniline (2.0 g, 10.0 mmol) and pyridine (6.4 mL, 79.3 mmol) in DCM (40 mL) at 0° C. After warming to room temperature the mixture is stirred for 3 hours. Water was added and the mixture washed with 6M HCl. The organic layer was dried over MgSO$_4$, filtered and evaporated to give a residue, which is purified by column chromatography on silica gel eluting with 15% EtOAc/heptane to give the title compound: (1.5 g) $^1$HNMR (DMSO-$d_6$): 7.28 (1H), 6.98 (1H), 6.45 (1H), 2.99 (3H), 2.31 (6H).

Step 2 Preparation of N-[3,4-dimethyl-5-(tributylstannanyl)phenyl]methanesulfonamide

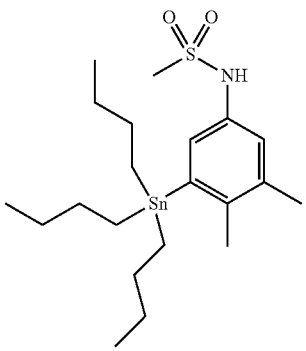 [SMILES: CCC[CH2][Sn]([CH2]CCC)([CH2]CCC)[c]1cc(NS(C)(=O)=O)cc(C)c1C]

Following the general procedure of Example 7—Step 1, and making non-critical variations but using product of Step 1 (Example 14), the title compound is obtained: (0.8 g) m/z (CI) 486 [M−H].

Example 15

Preparation of (6R,7R)-7-{[(2Z)-2-(2-amino-1,3-thiazol-4-yl)-2-(methoxyimino)acetyl]amino}-3-{2,4-dimethyl-5-[(methylsulfonyl)amino]benzyl}-8-oxo-5-thia-1-azabicyclo[4.2.0]oct-2-ene-2-carboxylic acid

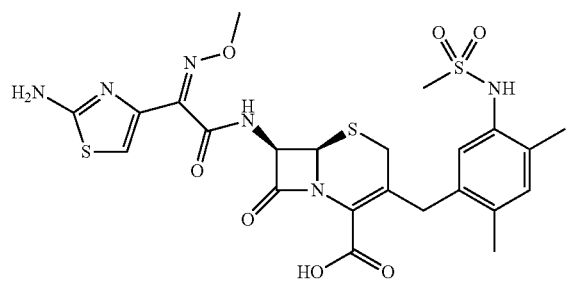 [SMILES: CO/N=C(\C(=O)N[C@@H]1C(=O)N2C(C(=O)O)=C(Cc3cc(NS(C)(=O)=O)c(C)cc3C)CS[C@H]12)c1csc(N)n1]

Following the general procedure of Example 14, and making non-critical variations but using commercially available 5-bromo-2,4-dimethylaniline as an intermediate the title compound is obtained. $^1$HNMR (DMSO-$d_6$): 9.59 (1H), 8.94 (1H), 7.03-7.05 (2H), 6.76 (1H), 5.72 (1H), 5.15 (1H), 3.84 (1H), 3.83 (3H), 3.70 (1H), 3.39 (1H), 3.29 (1H), 2.92 (3H), 2.24 (3H), 2.18 (3H). m/z (CI) 595 [M+H]$^+$.

Example 16

Preparation of (6R,7R)-7-{[(2Z)-2-(2-amino-1,3-thiazol-4-yl)-2-(methoxyimino)acetyl]amino}-3-{3-[methyl(methylsulfonyl)amino]benzyl}-8-oxo-5-thia-1-azabicyclo[4.2.0]oct-2-ene-2-carboxylic acid

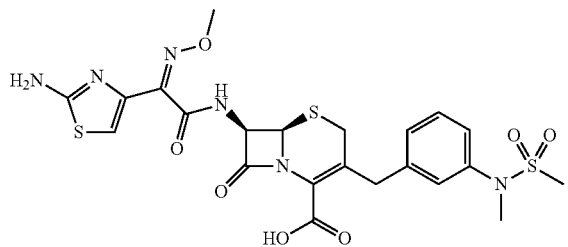 [SMILES: CO/N=C(\C(=O)N[C@@H]1C(=O)N2C(C(=O)O)=C(Cc3cccc(N(C)S(C)(=O)=O)c3)CS[C@H]12)c1csc(N)n1]

Following the general procedure of Example 14 and making non-critical variations but using N-(3-bromophenyl)-N-methylmethanesulfonamide (described in WO06015829) as an intermediate, the title compound is obtained. $^1$HNMR (DMSO-$d_6$): 9.55 (1H), 7.20-7.31 (3H), 7.14 (1H), 6.69 (1H), 5.65 (1H), 5.10 (1H), 3.85 (1H), 3.75-3.78 (4H), 3.41-3.54 (2H), 3.15 (3H), 2.87 (3H). m/z (CI) 581 [M+H]$^+$.

Example 17

Preparation of (6R,7R)-7-{[(2Z)-2-(2-amino-1,3-thiazol-4-yl)-2-(methoxyimino)acetyl]amino}-3-{3-[(methylsulfonyl)amino]benzyl}-8-oxo-5-thia-1-azabicyclo[4.2.0]oct-2-ene-2-carboxylic acid

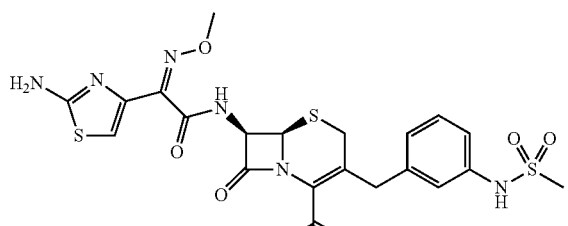

Following the general procedure of Example 14, and making non-critical variations but using commercially available N-(3-bromophenyl)methanesulfonamide as an intermediate, the title compound is obtained. $^1$HNMR (DMSO-$d_6$): 9.73 (1H), 9.63 (1H), 7.26 (1H), 7.14 (1H), 7.07 (1H), 7.00 (1H), 5.72 (1H), 5.16 (1H), 3.91 (1H), 3.85 (3H), 3.60 (1H), 3.48 (1H), 3.20 (1H), 2.99 (3H). m/z (CI) 580 [M+H]$^+$.

Example 18

Preparation of (6R,7R)-7-{[(2Z)-2-(2-amino-1,3-thiazol-4-yl)-2-(methoxyimino)acetyl]amino}-3-{3-methoxy-5-[(methylsulfonyl)amino]benzyl}-8-oxo-5-thia-1-azabicyclo[4.2.0]oct-2-ene-2-carboxylic acid

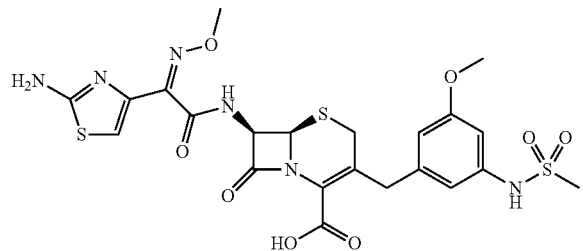 [SMILES: CO/N=C(\C(=O)N[C@@H]1C(=O)N2C(C(=O)O)=C(Cc3cc(NS(C)(=O)=O)cc(OC)c3)CS[C@H]12)c1csc(N)n1]

Following the general procedure of Example 14, and making non-critical variations but using commercially available 3-bromo-5-methoxyaniline, the title compound is obtained. LCMS: m/z (CI) 597 ([M+H]+.

Example 19

Preparation of (6R,7R)-7-{[(2Z)-2-(2-amino-1,3-thiazol-4-yl)-2-(methoxyimino)acetyl]amino}-3-{3-methyl-5-[(methylsulfonyl)amino]benzyl}-8-oxo-5-thia-1-azabicyclo[4.2.0]oct-2-ene-2-carboxylic acid

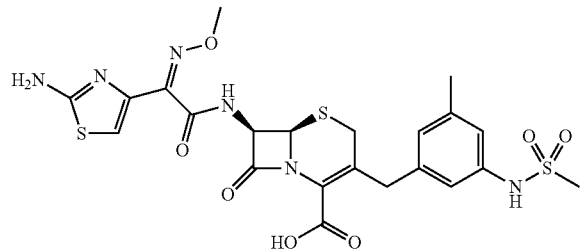 [SMILES: CO/N=C(\C(=O)N[C@@H]1C(=O)N2C(C(=O)O)=C(Cc3cc(C)cc(NS(C)(=O)=O)c3)CS[C@H]12)c1csc(N)n1]

Following the general procedure of Example 14, and making non-critical variations but using commercially available 3-bromo-5-methylaniline, the title compound is obtained.

$^1$HNMR (DMSO-$d_6$): 9.65 (1H), 6.95 (1H), 6.89 (1H), 6.82 (2H), 5.73-5.68 (1H), 5.16 (1H), 3.90-3.81 (4H), 3.58 (1H), 3.46 (1H), 3.21 (1H), 2.97 (3H), 2.25 (3H). m/z (CI) 581 [M+1]+.

Example 20

Preparation of (6R,7R)-3-(5-{[2-(acetylsulfanyl)ethyl]sulfamoyl}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxyl is acid

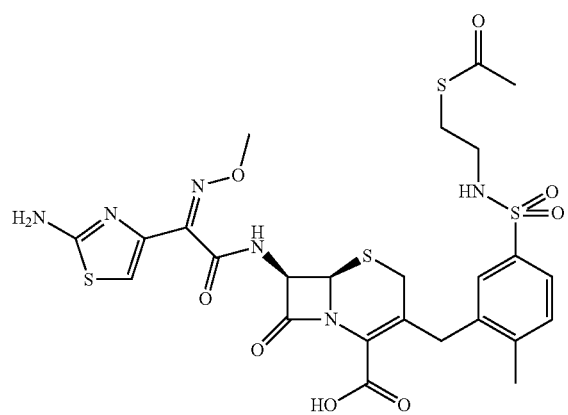 [SMILES: CO/N=C(\C(=O)N[C@@H]1C(=O)N2C(C(=O)O)=C(Cc3cc(S(=O)(=O)NCCSC(C)=O)ccc3C)CS[C@H]12)c1csc(N)n1]

Following the general procedure of Example 1, Steps 2-5, and making non-critical variations but using the product of Step 2, Example 20 as an intermediate, the title compound is obtained. $^1$HNMR (DMSO-$d_6$): 9.63 (1H), 7.76 (1H), 7.58 (2H), 7.4 (1H), 6.76 (1H), 5.74 (1H), 5.17 (1H), 3.8-4.0 (4H), 3.25 (2H), 2.85 (4H), 2.3 (6H). m/z (CI) 669 [M+H]+.

Step 1 Preparation of 3-bromo-N-(2-hydroxyethyl)-4-methylbenzenesulfonamide

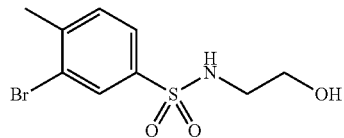

Ethanolamine (3.67 g, 60.1 mmol) is added to a solution of commercially available 3-bromo-4-methylbenzenesulfonyl chloride (13.5 g, 50.1 mmol) in THF (100 mL) at 0° C. After stirring for 1 hour the mixture is washed with brine, dried over magnesium sulfate, filtered and evaporated to give the title compound: (12.5 g) m/z (CI) 295 [M+1]+.

Step 2 Preparation of N-(2-hydroxyethyl)-4-methyl-3-(tributylstannanyl)benzenesulfonamide

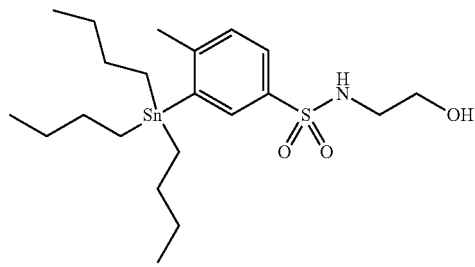 [SMILES: CCC[CH2][Sn]([CH2]CCC)([CH2]CCC)[c]1cc(S(=O)(=O)NCCO)ccc1C]

Following the general procedure of Example 7—Step 1, and making non-critical variations but using the product of Step 1, Example 20 as an intermediate, the title compound is obtained: (0.72 g) m/z (CI) 505 [M+H]+.

Example 21

Preparation of (6R,7R)-3-(3-{[2-(acetylsulfanyl)ethyl](ethyl)sulfamoyl}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid

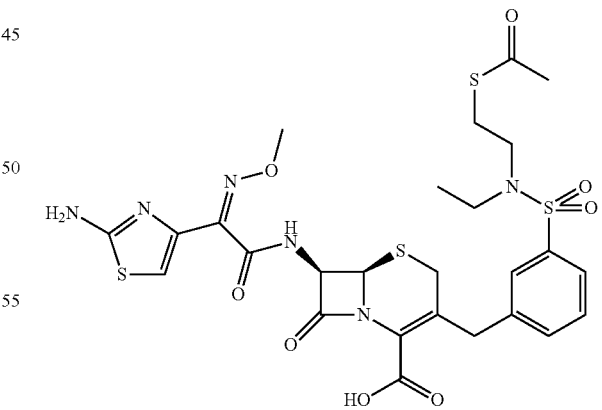

Following the general procedure of Example 20, and making non-critical variations but using commercially available 3-bromobenzenesulfonyl chloride and commercially available 2-(Ethylamino)ethanol, the title compound is obtained. (230 mg) $^1$HNMR (DMSO-$d_6$): 9.57 (1H), 7.5-7.8 (4H), 6.77 (1H), 6.83 (0.3H), 5.75 (0.7H), 5.55 (0.3H), 5.18 (1H), 4.28 (2H), 4.03 (0.7H), 3.84 (3H), 3.4-3.7 (4H), 3.17 (6H), 1.01 (3H). m/z (CI) 703 [M+Na]+.

Example 22

Preparation of (6R,7R)-7-{[(2Z)-2-(2-amino-1,3-thiazol-4-yl)-2-(methoxyimino)acetyl]amino}-3-[2-methoxy-5-(methylsulfamoyl)benzyl]-8-oxo-5-thia-1-azabicyclo[4.2.0]oct-2-ene-2-carboxylic acid

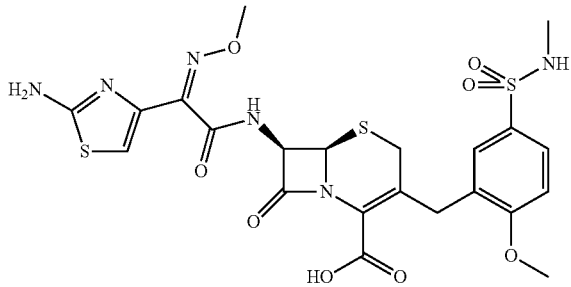 [SMILES: CNS(=O)(=O)c1ccc(OC)c(CC2=C(C(=O)O)N3C(=O)[C@@H](NC(=O)/C(=N\OC)c4csc(N)n4)[C@H]3SC2)c1]

Following the general procedure of Example 14, and making non-critical variations but using 3-bromo-4-methoxy-N-methylbenzenesulfonamide (described in WO05073244) as an intermediate, the title compound is obtained. $^1$HNMR (DMSO-d$_6$): 9.66 (1H), 7.83-7.36 (4H), 6.80 (1H), 5.78-5.72 (1H), 5.19 (1H), 4.03 (1H), 3.85 (3H), 3.70 (1H), 3.52 (1H). 3.19 (1H), 2.41 (3H). m/z (CI) 567 [M+1]$^+$.

Example 23

Preparation of (6R,7R)-7-{[(2Z)-2-(2-amino-1,3-thiazol-4-yl)-2-(methoxyimino)acetyl]amino}-3-[3-(methylsulfamoyl)benzyl]-8-oxo-5-thia-1-azabicyclo[4.2.0]oct-2-ene-2-carboxylic acid

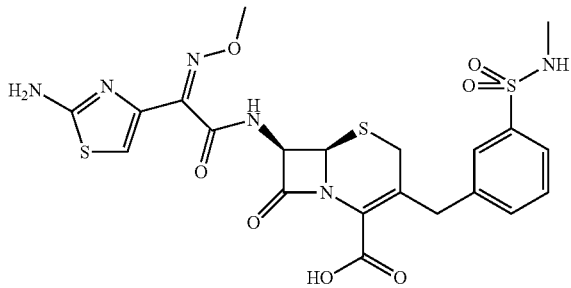 [SMILES: CNS(=O)(=O)c1cccc(CC2=C(C(=O)O)N3C(=O)[C@@H](NC(=O)/C(=N\OC)c4csc(N)n4)[C@H]3SC2)c1]

Following the general procedure of Example 14, and making non-critical variations but using commercially available 3-bromo-N-methylbenzenesulfonamide as an intermediate, the title compound is obtained. $^1$HNMR (DMSO-d$_6$): 9.66 (1H), 7.83-7.36 (4H), 6.80 (1H), 5.78-5.72 (1H), 5.19 (1H), 4.03 (1H), 3.85 (3H), 3.70 (1H), 3.52 (1H). 3.19 (1H), 2.41 (3H). m/z (CI) 567 [M+1]$^+$.

Example 24

Preparation of (6R,7R)-7-{[(2Z)-2-(2-amino-1,3-thiazol-4-yl)-2-(methoxyimino)acetyl]amino}-3-[2-methyl-5-(methylsulfamoyl)benzyl]-8-oxo-5-thia-1-azabicyclo[4.2.0]oct-2-ene-2-carboxylic acid

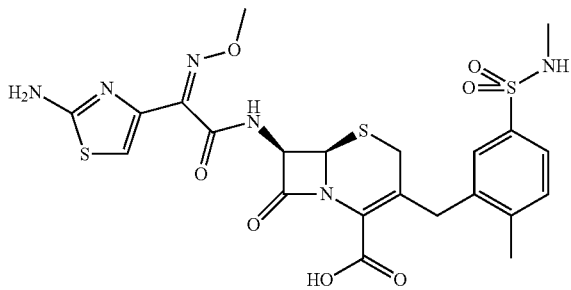 [SMILES: CNS(=O)(=O)c1ccc(C)c(CC2=C(C(=O)O)N3C(=O)[C@@H](NC(=O)/C(=N\OC)c4csc(N)n4)[C@H]3SC2)c1]

Following the general procedure of Example 14, and making non-critical variations but using commercially available 3-bromo-N-4-dimethylbenzenesulfonamide as an intermediate, the title compound is obtained. $^1$HNMR (DMSO-d$_6$): 9.59 (1H), 7.49 (1H), 7.33 (1H), 7.25 (1H), 6.69 (1H), 5.70-5.63 (1H), 5.11 (1H), 3.87 (1H), 3.76 (3H), 3.70 (1H), 3.28 (1H). 3.13 (1H), 2.32 (3H), 2.25 (3H). m/z (CI) 581 [M+1]$^+$.

Example 25

Preparation of (6R,7R)-7-{[(2Z)-2-(2-amino-1,3-thiazol-4-yl)-2-(methoxyimino)acetyl]amino}-3-[3-(dimethylsulfamoyl)benzyl]-8-oxo-5-thia-1-azabicyclo[4.2.0]oct-2-ene-2-carboxylic acid

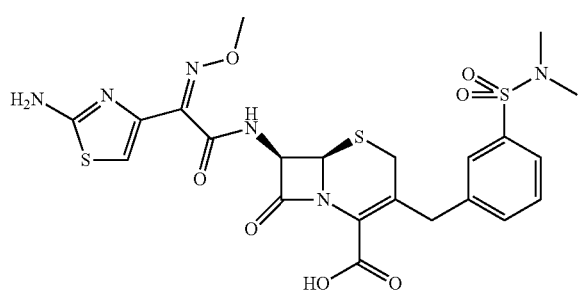 [SMILES: CO/N=C(\C(=O)N[C@@H]1C(=O)N2C(C(=O)O)=C(Cc3cccc(S(=O)(=O)N(C)C)c3)CS[C@H]12)c1csc(N)n1]

Following the general procedure of Example 20, and making non-critical variations but using commercially available 3-bromo-N,N-dimethylbenzenesulfonamide as an intermediate, the title compound is obtained. $^1$HNMR (DMSO-d$_6$): 9.68 (1H), 7.70 (1H), 7.64-7.60 (3H), 6.81 (1H), 5.77-5.72 (1H), 5.18 (1H), 4.04 (1H), 3.88 (3H), 3.73 (1H), 3.55 (1H). 3.20 (1H), 2.59 (6H). m/z (CI) 581 [M+1]$^+$.

Example 26

Preparation of (6R,7R)-7-{[(2Z)-2-(2-amino-1,3-thiazol-4-yl)-2-(methoxyimino)acetyl]amino}-3-[3-methoxy-5-(methylsulfamoyl)benzyl]-8-oxo-5-thia-1-azabicyclo[4.2.0]oct-2-ene-2-carboxylic acid

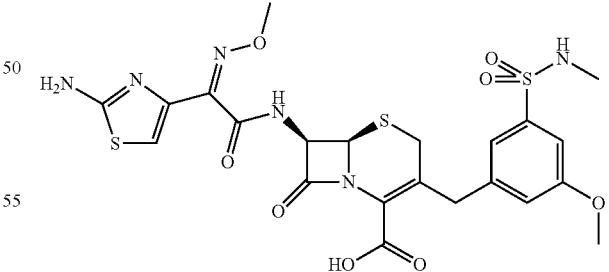

Following the general procedure of Example 20, and making non-critical variations but using commercially available 3-bromo-5-methoxybenzenesulfonyl chloride and commercially available N-methylamine, the title compound is obtained. $^1$HNMR (DMSO-d$_6$): 9.67 (1H), 7.31 (1H), 7.16 (1H), 7.11 (1H), 6.80 (1H), 5.77-5.71 (1H), 5.19 (1H), 3.98 (1H), 3.85 (3H), 3.81 (3H), 3.67 (1H), 3.53 (1H), 3.21 (1H), 2.42 (3H). m/z (CI) 597 [M+1]$^+$.

Example 27

Preparation of (6R,7R)-7-{[(2Z)-2-(2-amino-1,3-thiazol-4-yl)-2-(methoxyimino)acetyl]amino}-3-[3-methyl-5-(methylsulfamoyl)benzyl]-8-oxo-5-thia-1-azabicyclo[4.2.0]oct-2-ene-2-carboxylic acid

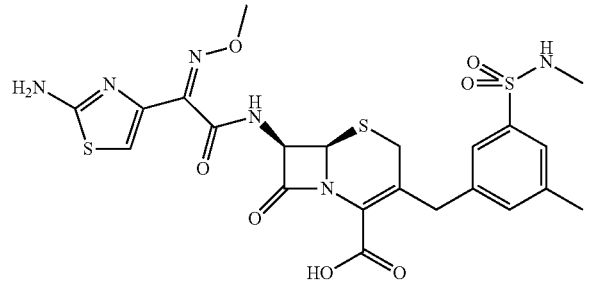 [SMILES: CNS(=O)(=O)c1cc(C)cc(CC2=C(C(=O)O)N3C(=O)[C@@H](NC(=O)/C(=N\OC)c4csc(N)n4)[C@H]3SC2)c1]

Following the general procedure of Example 20, and making non-critical variations but using commercially available 3-bromo-N,5-dimethylbenzenesulfonamide as an intermediate, the title compound is obtained. $^1$HNMR (DMSO-$d_6$): 9.56 (1H), 7.45 (1H), 7.40 (1H), 7.28 (1H), 6.69 (1H), 5.69-5.5.63 (1H), 5.10 (1H), 3.91 (1H), 3.76 (3H), 3.53 (1H), 3.43 (1H), 3.13 (1H) 2.32 (3H). m/z (CI) 581 [M+1]$^+$.

Example 28

Preparation of (6R,7R)-7-{[(2Z)-2-(2-amino-1,3-thiazol-4-yl)-2-(methoxyimino)acetyl]amino}-3-[2-methyl-4-(methylsulfonyl)benzyl]-8-oxo-5-thia-1-azabicyclo[4.2.0]oct-2-ene-2-carboxylic acid

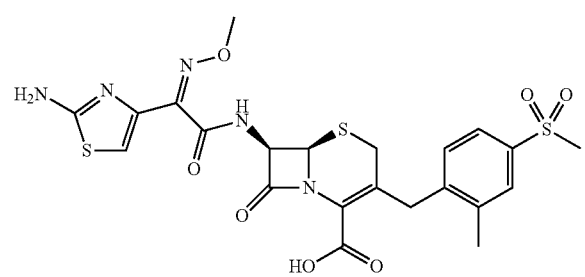 [SMILES: CO/N=C(\C(=O)N[C@@H]1C(=O)N2C(C(=O)O)=C(Cc3ccc(S(C)(=O)=O)cc3C)CS[C@H]12)c1csc(N)n1]

Following the general procedure of Example 1—Steps 2 and 5, and making non-critical variations but using the product of Step 2, Example 27 as an intermediate, the title compound is obtained. $^1$HNMR (DMSO-$d_6$): 9.65 (1H), 7.75 (1H), 7.69 (1H), 7.31 (1H), 6.78 (1H), 5.75 (1H), 5.21 (1H), 3.85 (3H), 4.05-4.40 (2H), 3.45 (1H), 3.18-3.24 (4H), 2.36 (3H). m/z (CI) 566 [M+H]$^+$.

Step 1 Preparation of tributyl[2-methyl-4-(methylsulfonyl)phenyl]stannane

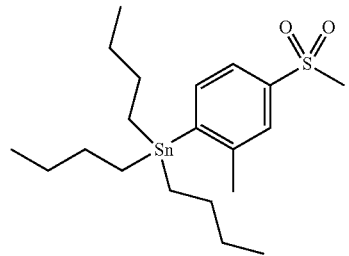 [SMILES: CCC[CH2][Sn]([CH2]CCC)([CH2]CCC)[c]1ccc(S(C)(=O)=O)cc1C]

Following the general procedure of Example 7—Step 1, and making non-critical variations but using 1-bromo-2-methyl-4-(methylsulfonyl)benzene (described in WO08030466) as an intermediate, the title compound is obtained: (4.9 g) m/z (CI) 461 [M+H]$^+$.

What is claimed is:
1. A compound of formula I

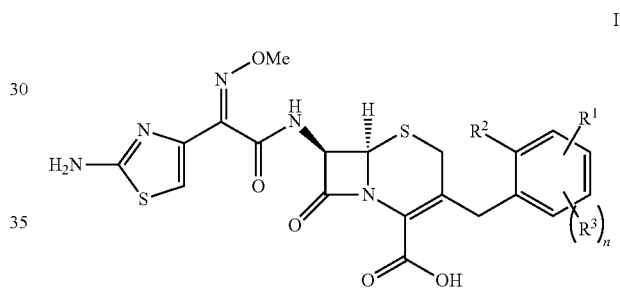

or a pharmaceutically acceptable salt thereof wherein:
$R^1$ is —$NR^4R^5$, —$SO_2R^6$, —$C(=O)NR^4R^4$, —$SR^4$, —$S(C=O)R^4$, —$C_{1-4}$alkyl substituted with —$SR^4$, —$S(C=O)R^4$, —(=O)$NR^4R^5$, or —$SO_2R^6$; or $R^1$ is —$OC_{1-8}$alkyl substituted with —$SR^4$, —$S(C=OR^4$, —$C(=O)NR^4R^5$, or —$SO_2R^6$;

$R^2$ and $R^3$ are independently —H, —OH, —CN, halo, —$NO_2$, —$C_{1-10}$alkyl, —$OC_{1-10}$alkyl, —$N(R^4)_2$;

$R^4$ is —H or —$C_{1-10}$alkyl;

$R^5$ is —$SO_2R^{4'}$, —$C(=)C_{1-10}$alkyl;

$R^6$ is H, $C_{1-6}$alkyl, or $NR^4R^4$;

at each occurrence, $C_{1-10}$alkyl is optionally substituted with —OH, —CN, halo, —$NO_2$, —$OC_{1-6}$alkyl, —SH, —$SC_{1-4}$alkyl, —$S(C=O)C_{1-4}$alkyl, or —$O(C=O)C_{1-4}$alkyl; and n is 1, 2, or 3.

2. A compound of claim 1 wherein $R^1$ is —$NR^4R^5$, —$SO_2R^6$, or —$C_{1-4}$alkyl substituted with —$SR^4$, —$S(C=O)R^4$, —$C(=O)NR^4R^5$, or —$SO_2R^6$.

3. A compound of claim 1 wherein $R^1$ is —$C_{1-4}$alkyl substituted with —$SR^4$, —$S(C=O)R^4$, or —$SO_2R^6$.

4. A compound of claim 1 wherein $R^1$ is a methyl substituted with —$SR^4$, —$S(C=O)R^4$, or —$SO_2R^6$.

5. A compound of claim 1 wherein $R^1$ is a methyl substituted with —SH, or —$S(C=O)CH_3$.

6. A compound of claim 2 wherein $R^1$ is —$NHC_{1-6}$alkyl substituted with —SH, —$SC_{1-4}$alkyl, or —$S(C=O)C_{1-4}$alkyl.

7. A compound of claim 1 wherein $R^2$ is H or $C_{1-4}$alkyl.

8. A compound of claim 1 wherein $R^2$ is $C_{1-4}$alkyl.

9. A compound of claim 1 wherein $R^3$ is H, OH, or $C_{1-6}$alkyl optionally substituted with OH, CN, halo, $NO_2$, $OC_{1-6}$alkyl, SH, $SC_{1-4}$alkyl, $S(C=O)C_{1-4}$alkyl, or —$O(C=O)C_{1-4}$alkyl.

10. A compound of claim 1 wherein $R^3$ is H or $C_{1-4}$alkyl optionally substituted with OH, $OC_{1-4}$alkyl, SH, or $SC_{1-4}$alkyl.

11. A compound of claim 1 wherein $R^1$ is —$NR^4R^5$, —$SO_2R^6$, —$C(=O)NR^4R^4$, —$SR^4$, —$S(C=O)R^4$, —$C_{1-4}$alkyl substituted with —$SR^4$, —$S(C=O)R^4$, —$C(=O)NR^4R^5$, or —$SO_2R^6$; or $R^1$ is —$OC_{1-8}$alkyl substituted with —$SR^4$, —$S(C=O)R^4$, —$C(=O)NR^4R^5$, or —$SO_2R^6$; $R^2$ is H or $C_{1-4}$alkyl; and $R^3$ is H or $C_{1-4}$alkyl optionally substituted with OH, $OC_{1-4}$alkyl, SH, or $SC_{1-4}$alkyl.

12. A compound of claim 1 wherein $R^1$ is —$NR^4R^5$, —$SO_2R^6$, or —$C_{1-4}$alkyl substituted with —$SR^4$, —$S(C=O)R^4$, —$C(=O)NR^4R^5$, or —$SO_2R^6$; $R^2$ is H or $C_{1-4}$alkyl; and $R^3$ is H or $C_{1-4}$alkyl optionally substituted with OH, $OC_{1-4}$alkyl, SH, or $SC_{1-4}$alkyl.

13. A compound of claim 1 wherein $R^1$ is —$C_{1-4}$alkyl substituted with —$SR^4$, —$S(C=O)R^4$, or —$SO_2R^6$; $R^2$ is H or $C_{1-4}$alkyl; and $R^3$ is H or $C_{1-4}$alkyl.

14. A compound of claim 1 wherein $R^1$ is a methyl substituted with —SH, or —$S(C=O)CH_3$; $R^2$ is H or $C_{1-4}$alkyl; and $R^3$ is H or $C_{1-4}$alkyl.

15. A compound of claim 1 wherein $R^1$ is a methyl substituted with —SH, or —$S(C=O)CH_3$; $R^2$ is H or methyl; and $R^3$ is H or methyl.

16. A compound of claim 1 which is 1) (6R,7R)-3-{3-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

2) (6R,7R)-3-{4-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

3) (6R,7R)-3-{5-[(acetylsulfanyl)methyl]-2-methylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

4) (6R,7R)-3-{3-[(acetylsulfanyl)methyl]-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

5) (6R,7R)-3-{3-[(acetylsulfanyl)methyl]-5-(hydroxymethyl)-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

6) (6R,7R)-3-{4-[(acetylsulfanyl)methyl]-2,6-dimethylbenzyl}-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

7) (6R,7R)-3-(3-{[(acetylsulfanyl)acetyl]amino}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

8) (6R,7R)-3-(5-{[(acetylsulfanyl)acetyl]amino}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

9) (6R,7R)-3-(4-{[(acetylsulfanyl)acetyl](propyl)amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

10) (6R,7R)-3-(3-{[(acetylsulfanyl)acetyl](methyl)amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

11) (6R,7R)-7-{[(2Z)-2-(2-amino-1,3-thiazol-4-yl)-2-(methoxyimino)acetyl]amino}-3-(3-{[(methylsulfanyl)acetyl]amino}benzyl)-8-oxo-5-thia-1-azabicyclo[4.2.0]oct-2-ene-2-carboxylic acid;

12) (6R,7R)-3-(3-{[(acetylsulfanyl)acetyl]amino}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

13) (6R,7R)-7-{[(2Z)-2-(2-amino-1,3-thiazol-4-yl)-2-(methoxyimino)acetyl]amino}-8-oxo-3-{3-[propan-2-yl(sulfanylacetyl)amino]benzyl}-5-thia-1-azabicyclo[4.2.0]oct-2-ene-2-carboxylic acid;

14) (6R,7R)-7-{[(2Z)-2-(2-amino-1,3-thiazol-4-yl)-2-(methoxyimino)acetyl]amino}-3-{2,3-dimethyl-5-[(methylsulfonyl)amino]benzyl}-8-oxo-5-thia-1-azabicyclo[4.2.0]oct-2-ene-2-carboxylic acid;

15) (6R,7R)-7-{[(2Z)-2-(2-amino-1,3-thiazol-4-yl)-2-(methoxyimino)acetyl]amino}-3-{2,4-dimethyl-5-[(methylsulfonyl)amino]benzyl}-8-oxo-5-thia-1-azabicyclo[4.2.0]oct-2-ene-2-carboxylic acid;

16) (6R,7R)-7-{[(2Z)-2-(2-amino-1,3-thiazol-4-yl)-2-(methoxyimino)acetyl]amino}-3-{3-[methyl(methylsulfonyl)amino]benzyl}-8-oxo-5-thia-1-azabicyclo[4.2.0]oct-2-ene-2-carboxylic acid;

17) (6R,7R)-7-{[(2Z)-2-(2-amino-1,3-thiazol-4-yl)-2-(methoxyimino)acetyl]amino}-3-{3-[(methylsulfonyl)amino]benzyl}-8-oxo-5-thia-1-azabicyclo[4.2.0]oct-2-ene-2-carboxylic acid;

18) (6R,7R)-7-{[(2Z)-2-(2-amino-1,3-thiazol-4-yl)-2-(methoxyimino)acetyl]amino}-3-{3-methoxy-5-[(methylsulfonyl)amino]benzyl}-8-oxo-5-thia-1-azabicyclo[4.2.0]oct-2-ene-2-carboxylic acid;

19) (6R,7R)-7-{[(2Z)-2-(2-amino-1,3-thiazol-4-yl)-2-(methoxyimino)acetyl]amino}-3-{3-methyl-5-[(methylsulfonyl)amino]benzyl}-8-oxo-5-thia-1-azabicyclo[4.2.0]oct-2-ene-2-carboxylic acid;

20) (6R,7R)-3-(5-{[2-(acetylsulfanyl)ethyl]sulfamoyl}-2-methylbenzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

21) (6R,7R)-3-(3-{[2-(acetylsulfanyl)ethyl](ethyl)sulfamoyl}benzyl)-7-{[(2Z)-2-(2-amino-1,3-thiazol-4-yl)-2-(methoxyimino)acetyl]amino}-8-oxo-5-thia-1-azabicyclo[4.2.0]oct-2-ene-2-carboxylic acid;

22) (6R,7R)-7-{[(2Z)-2-(2-amino-1,3-thiazol-4-yl)-2-(methoxyimino)acetyl]amino}-3-[2-methoxy-5-(methylsulfamoyl)benzyl]-8-oxo-5-thia-1-azabicyclo[4.2.0]oct-2-ene-2-carboxylic acid;

23) (6R,7R)-7-{[(2Z)-2-(2-amino-1,3-thiazol-4-yl)-2-(methoxyimino)acetyl]amino}-3-[3-(methylsulfamoyl)benzyl]-8-oxo-5-thia-1-azabicyclo[4.2.0]oct-2-ene-2-carboxylic acid;

24) (6R,7R)-7-{[(2Z)-2-(2-amino-1,3-thiazol-4-yl)-2-(methoxyimino)acetyl]amino}-3-[2-methyl-5-(methylsulfamoyl)benzyl]-8-oxo-5-thia-1-azabicyclo[4.2.0]oct-2-ene-2-carboxylic acid;

25) (6R,7R)-7-{[(2Z)-2-(2-amino-1,3-thiazol-4-yl)-2-(methoxyimino)acetyl]amino}-3-[3-(dimethylsulfamoyl)benzyl]-8-oxo-5-thia-1-azabicyclo[4.2.0]oct-2-ene-2-carboxylic acid;

26) (6R,7R)-7-{[(2Z)-2-(2-amino-1,3-thiazol-4-yl)-2-(methoxyimino)acetyl]amino}-3-[3-methoxy-5-(methylsulfamoyl)benzyl]-8-oxo-5-thia-1-azabicyclo[4.2.0]oct-2-ene-2-carboxylic acid;

27) (6R,7R)-7-{[(2Z)-2-(2-amino-1,3-thiazol-4-yl)-2-(methoxyimino)acetyl]amino}-3-[3-methyl-5-(methylsulfamoyl)benzyl]-8-oxo-5-thia-1-azabicyclo[4.2.0]oct-2-ene-2-carboxylic acid; or 28) (6R,7R)-7-{[(2Z)-2-(2-amino-1,3-thiazol-4-yl)-2-(methoxyimino)acetyl]amino}-3-[2-methyl-4-(methylsulfonyl)benzyl]-8-oxo-5-thia-1-azabicyclo[4.2.0]oct-2-ene-2-carboxylic acid.

17. A pharmaceutical composition comprising a compound of claim 1, or a pharmaceutically acceptable salt thereof and a pharmaceutically acceptable carrier.

* * * * *